(12) United States Patent
Mettauer et al.

(10) Patent No.: US 11,998,706 B2
(45) Date of Patent: Jun. 4, 2024

(54) INTEGRATED CATHETER ASSEMBLY

(71) Applicant: Evolve Medicus, Inc., Gainesville, FL (US)

(72) Inventors: Mark Menefee Mettauer, The Woodlands, TX (US); Steve Lepke, Wakefield, MA (US)

(73) Assignee: EVOLVE MEDICUS, INC., Gainesville, FL (US)

( * ) Notice: Subject to any disclaimer, the term of this patent is extended or adjusted under 35 U.S.C. 154(b) by 0 days.

(21) Appl. No.: 18/235,873

(22) Filed: Aug. 20, 2023

(65) Prior Publication Data

US 2023/0398329 A1 Dec. 14, 2023

Related U.S. Application Data

(63) Continuation-in-part of application No. 18/101,645, filed on Jan. 26, 2023, now Pat. No. 11,826,519,
(Continued)

(51) Int. Cl.
*A61M 25/06* (2006.01)
*A61M 1/36* (2006.01)
(Continued)

(52) U.S. Cl.
CPC .... *A61M 25/0606* (2013.01); *A61M 25/0097* (2013.01); *A61M 25/02* (2013.01);
(Continued)

(58) Field of Classification Search
CPC .......... A61M 25/0606; A61M 25/0097; A61M 25/02; A61M 39/10; A61M 1/3661;
(Continued)

(56) References Cited

U.S. PATENT DOCUMENTS

| | | | | |
|---|---|---|---|---|
| 4,496,348 A | * | 1/1985 | Genese | A61M 25/0606 604/167.02 |
| 4,842,582 A | * | 6/1989 | Mahurkar | A61M 5/1582 604/115 |
| 4,957,488 A | * | 9/1990 | Cameron | A61M 25/0631 604/161 |
| 5,976,103 A | * | 11/1999 | Martin | A61M 25/0026 604/35 |
| 8,915,891 B2 | * | 12/2014 | Bornhoft | A61M 39/10 604/181 |

(Continued)

FOREIGN PATENT DOCUMENTS

| | | | | |
|---|---|---|---|---|
| BR | 112021000677 A2 | * | 4/2021 | ......... A61B 5/15003 |
| WO | WO-2006069424 A2 | * | 7/2006 | ........ A61M 25/0606 |

*Primary Examiner* — Susan S Su
*Assistant Examiner* — Ted Yang
(74) *Attorney, Agent, or Firm* — Marc Deflache; Jones Delflache LLP

(57) ABSTRACT

An integrated catheter assembly includes a housing member, an outer lumen member extending from the housing member, and a needle member having a needle slidably or movably coupled to the housing member, wherein the needle can be extended beyond the outer lumen. Once a flash of blood is confirmed the needle member is uncoupled from the housing member and removed from within the patient's vein or artery. A non-removable inner lumen member is connected to the housing member. The distal end of the outer lumen is sealed against the distal end of the inner lumen and includes at having at least one aperture to transfer blood out of the patient to the dialysis machine. The integrated catheter assembly therefore receives and delivers blood through a single injection site.

16 Claims, 41 Drawing Sheets

Related U.S. Application Data which is a continuation-in-part of application No. 17/396,837, filed on Aug. 9, 2021, now Pat. No. 11,759,611.

(51) Int. Cl.
*A61M 25/00* (2006.01)
*A61M 25/02* (2006.01)
*A61M 39/10* (2006.01)

(52) U.S. Cl.
CPC ............ *A61M 39/10* (2013.01); *A61M 1/3661* (2014.02); *A61M 2025/0031* (2013.01); *A61M 2025/0253* (2013.01)

(58) Field of Classification Search
CPC .. A61M 2025/0031; A61M 2025/0253; A61M 25/01; A61M 25/065; A61M 25/0693; A61M 2025/0687; A61M 2025/0681
See application file for complete search history.

(56) References Cited

U.S. PATENT DOCUMENTS

| | | | |
|---|---|---|---|
| 10,569,057 B2* | 2/2020 | White | A61M 25/0631 |
| 2006/0155244 A1* | 7/2006 | Popov | A61M 25/0625 |
| | | | 604/110 |
| 2008/0009784 A1* | 1/2008 | Leedle | A61M 1/3661 |
| | | | 604/43 |
| 2010/0076406 A1* | 3/2010 | Raulerson | A61M 25/0194 |
| | | | 604/528 |
| 2011/0282293 A1* | 11/2011 | Hordum | A61M 25/02 |
| | | | 604/180 |
| 2014/0221932 A1* | 8/2014 | Puhasmagi | A61M 1/3661 |
| | | | 604/167.05 |
| 2016/0296728 A1* | 10/2016 | Smith | A61M 25/0631 |
| 2019/0247090 A1* | 8/2019 | Armstrong | A61M 25/09041 |
| 2019/0328954 A1* | 10/2019 | Hull | A61M 39/0247 |
| 2020/0023176 A1* | 1/2020 | Hu | A61B 5/6852 |
| 2021/0023336 A1* | 1/2021 | Lee | A61M 1/3661 |

\* cited by examiner

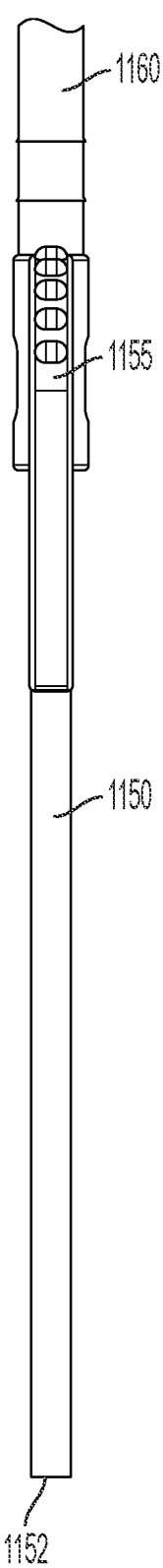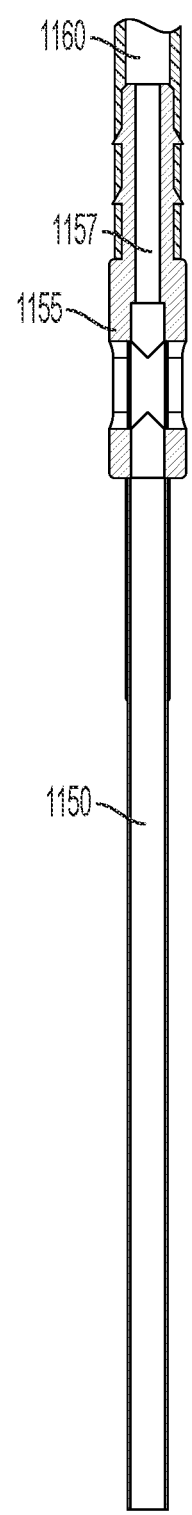
FIG. 23A FIG. 23B FIG. 23C

INTEGRATED CATHETER ASSEMBLY

RELATED APPLICATIONS

This application is a continuation-in-part of U.S. patent application Ser. No. 18/101,645, filed Jan. 26, 2023, entitled Integrated Catheter Assembly, which is a continuation-in-part of U.S. patent application Ser. No. 17/396,837, filed Aug. 9, 2021, also entitled Integrated Catheter Assembly, which foregoing applications are hereby incorporated by reference in their entirety and made a part of this Application.

FIELD OF THE INVENTION

The present general inventive concept relates to medical devices for dialysis and more particularly to an integrated catheter for dialysis.

BACKGROUND OF THE INVENTION

Injuries, diseases, or disorders can cause kidney or renal system failure, resulting in a variety of physiological problems. Levels of various fluids and minerals can exceed healthy ranges. Toxic byproducts of bodily processes can then accumulate in blood and tissues, leading to myriad long term negative health consequences.

The present state of the art for addressing kidney or renal system failure is to perform dialysis procedures that are designed to supplement or replace the body's own filtering functions. These procedures, to varying degrees, are effective at removing waste and toxins from the body when a patient's own renal system is unable to do so. Certain patients need more frequent or more extensive dialysis sessions than do others. Regardless, each session can be a mental and physical challenge, and discomfort associated with the procedure is to a significant degree related to the attachment of the patient to the dialysis machine.

For a hemodialysis procedure, a patient is attached to a hemodialysis machine using catheters, one of which removes blood from the patient and the other of which returns blood to the patient. The machine removes waste and toxins from the received blood and returns the filtered blood back to the patient. For each session, the patient must have the catheters inserted into a vein, artery, or surgically created arteriovenous fistula (or shunt), which is an unpleasant procedure, especially when undergone three times per week, which is a frequency of dialysis required for the majority of afflicted patients.

At present, the securing of catheters to the patient involves the following steps. The skin of a first insertion target area of the patient is cleaned, and a tourniquet is applied between the first insertion target area and the shoulder of the patient. A first needle is inserted into the arteriovenous fistula at the first insertion target area, and a flash of blood is observed to indicate that access to the shunt or arteriovenous fistula was successful. Then, the skin of a second insertion target area of the patient is cleaned, the first needle is secured to the arm of the patient using multiple rounds of tape, and the tube attached to the first needle is clamped to prevent blood flow out from the patient.

A second needle is inserted into the shunt or arteriovenous fistula at the second insertion target area, and a flash of blood is observed to indicate that access to the shunt or arteriovenous fistula was successful. The second needle is secured to the arm of the patient using multiple rounds of tape, and the tube attached to the second needle is clamped to prevent blood flow out from the patient.

Next, the tubes are primed, clamped, and attached to the dialysis machine. Loose portions of the tubes are taped to the patient's shoulder. Finally, the tube clamps and the tourniquet are removed. The dialysis machine then filters blood from the patient for the recommended time. Once the session is complete, the tape and multiple needles must be removed from the patient and hemostasis acquired.

As can easily be understood from even the above cursory description of the current process, the attachment of the patient to the dialysis machine is uncomfortable at best and painful at worst.

For the above reasons, there is a need for improved catheter devices and configurations, and particularly catheter devices and configurations that decrease discomfort and pain experienced by dialysis patients. The present invention addresses this need and provides additional benefits.

SUMMARY OF THE INVENTION

The present invention provides an integrated catheter assembly and methods of use.

As should be appreciated, the integrated catheter device of the present general inventive concept provides one or more of the following benefits.

Preferred embodiments provide an integrated, all-in-one device, and accordingly reduces confusion, misconfiguration, and the training required to effectively administer the procedure. The tubing management features of the device also contribute to these benefits.

Preferred embodiments increase comfort, at least by use of a 14 G needle that is retracted. It can be understood that a 14 G needle that is retracted is more comfortable than a 15 G needle that remains, as is the case with current catheters. This also increase the flow rate, which reduces the times needed for the dialysis process.

Preferred embodiments provide a single point of entry, reducing needle insertions from 2 to 1. This further reduces the time needed for the procedure and reduces the potential infection. The current procedure averages 4 hours and 17 minutes. With the present invention, the procedure can be shortened at least to 2 hours and 3 minutes. Based on 12 procedures per month, this reduces needle entries from 24 times to 12 times, and reduces procedure time by: 1 hour, 47 minutes per session, which is 5 hours and 21 minutes per week, which is 21 hours and 24 minutes per month, which is 11 days, 14 hours and 12 minutes per year. This also potentially lowers healthcare costs.

The above benefits and others can be realized by an integrated catheter assembly of the invention. Preferred embodiments of the present invention include a housing member having a first end and an opposing second end; an outer lumen member to extend from the first end of the housing member; and a needle member slidably (or movably) coupled to the housing member, wherein the needle member extends beyond the outer lumen member in a first position and is concealed in a second position.

In preferred embodiments, the catheter assembly further includes a locking feature to releasably lock the needle member at the first and second positions.

Further in preferred embodiments, the outer lumen member includes a plurality of ports in fluidic communication with each other, the plurality of ports including a first port disposed at a first end of the outer lumen member, a second port disposed at an opposing second end, and a third port disposed between the first port and the second port.

Preferably, the needle member includes a sharp tip at a first end and a blunt tip at an opposing second end. Further preferably, the needle member includes a relief port disposed between the first end and the second end. Still further preferably, fluid received by the needle member is diverted by the relief port to the third port when the needle member is disposed at the first position.

Preferably, the catheter assembly further includes a coupling body member attached to the second port of the outer lumen member and configured to receive an inner lumen. Further preferably, the catheter assembly further includes an inner lumen depth gauge coupled to the coupling body member. Still further preferably, the depth gauge includes depth markings, and the inner lumen includes an inner lumen depth marker cooperating with the depth markings to indicate a distance from which a first end of the inner lumen member extends past the first port of the outer lumen member.

Further preferably, when the inner lumen is disposed coaxial with the outer lumen and the needle is in the second position, blood flow is permitted between an outer wall of the inner lumen and an inner wall of the outer lumen. Still further preferably, the inner lumen has an outer diameter smaller than an inner diameter of the needle member and the needle member has an outer diameter smaller than an inner diameter of the outer lumen.

Further preferably, the catheter assembly further includes an outflow tube coupled in fluidic communication with the third port and an inflow tube coupled in fluidic communication with the inner lumen member. Still further preferably, the housing member includes at least one channel by which at least one of the tubes can be held adjacent the housing member.

Further preferably, outer surfaces of the housing member are non-parallel such that when the housing member is adjacent a target area of a patient, a longitudinal axis of the outer lumen member and a longitudinal axis of the inner lumen member are angled toward the target area. Still further preferably, the housing member includes at least one adhesive flap contoured to approximate a curvature of an arm.

A method of use of the integrated catheter assembly of preferred embodiments of the present invention includes a method of attaching a patient to a dialysis machine, including the steps of inserting into a target arteriovenous fistula of a patient a needle member coupled to a housing member of an integrated catheter assembly, the needle member extending from a first port of an outer lumen member extending from the housing member, the outer lumen member having a second port opposite the first port and configured to accept an inner lumen; observing a flash of blood at a third port of the outer lumen member, the third port positioned between the first and second ports, the blood having passed into the needle member, out a relief port of the needle member and into the third port of the outer lumen member; retracting the needle member into the outer lumen until blood flows into the first port and directly out the third port; inserting the inner lumen into the second port of the outer lumen until the inner lumen extends from the first port of the outer lumen and into the arteriovenous fistula; and connecting to the dialysis machine an outflow tube in fluidic communication with the third port of the outer lumen member, and an inflow tube in fluidic communication with the inner lumen member.

In preferred embodiments, the method further includes passing the inner lumen adjacent an inner lumen depth gauge. Preferably, the method further includes aligning a depth marker to a desired depth marking of the depth gauge to establish a desired distance from which a first end of the inner lumen member extends past the first port of the outer lumen member.

In preferred embodiments, the method further includes disposing the inner lumen coaxial with the outer lumen. Preferably, the inner lumen has an outer diameter smaller than an inner diameter of the needle member and the needle member has an outer diameter smaller than an inner diameter of the outer lumen.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

BRIEF DESCRIPTION OF THE DRAWINGS

FIGS. 23A, 23B, and 23C are views of the thumb slide housing and inner lumen shown in FIGS. 17A/B and 22A.

DETAILED DESCRIPTION OF PREFERRED EMBODIMENTS

Figure 1A:
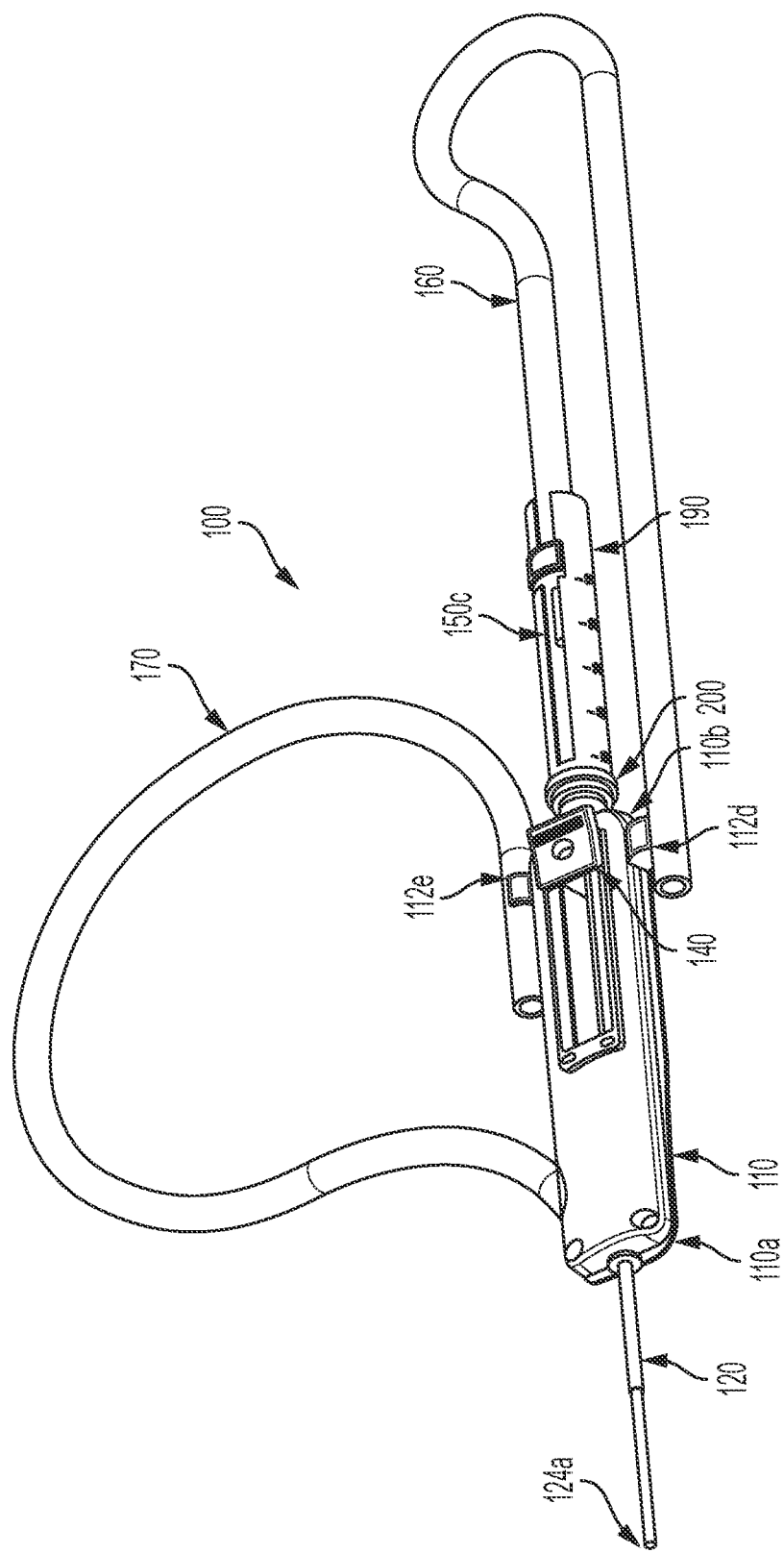
FIGS. 1A and 1B are front perspective views of an integrated catheter device according to an example of the present general inventive concept, showing a housing member with a needle member (not visible) retracted and an inner lumen member that cooperates with the housing member.
Figure 1B:
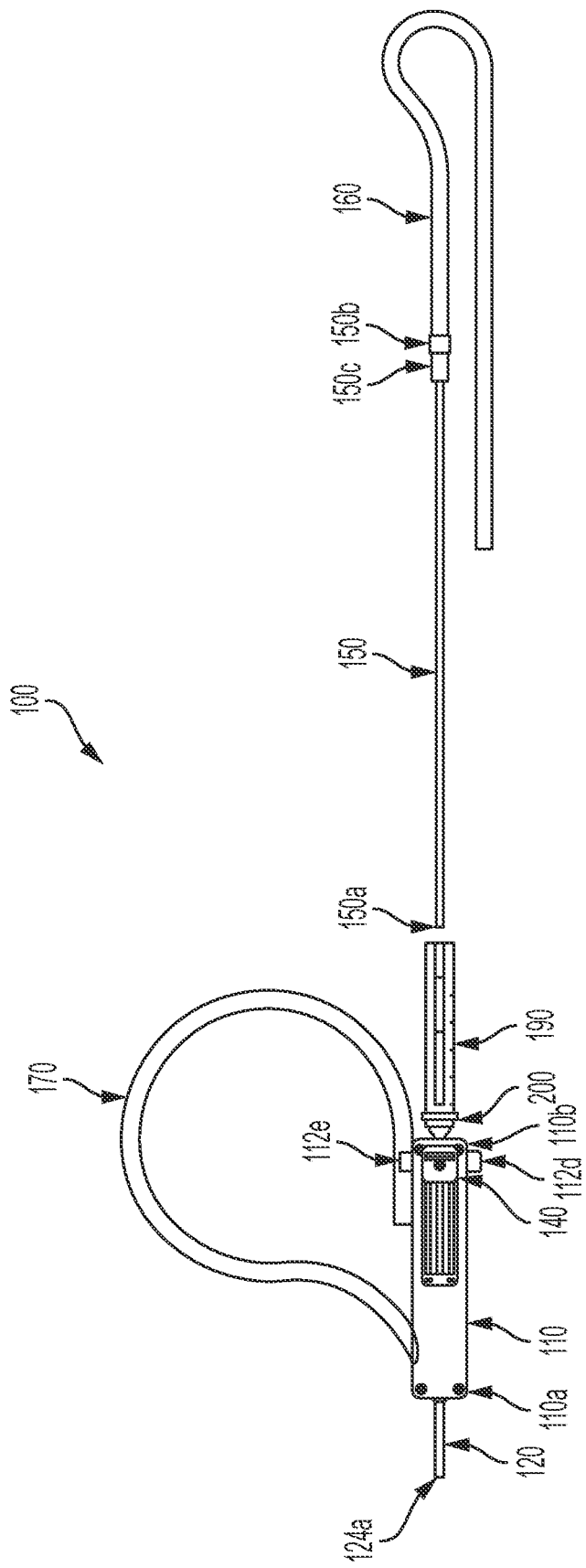
Figure 2:
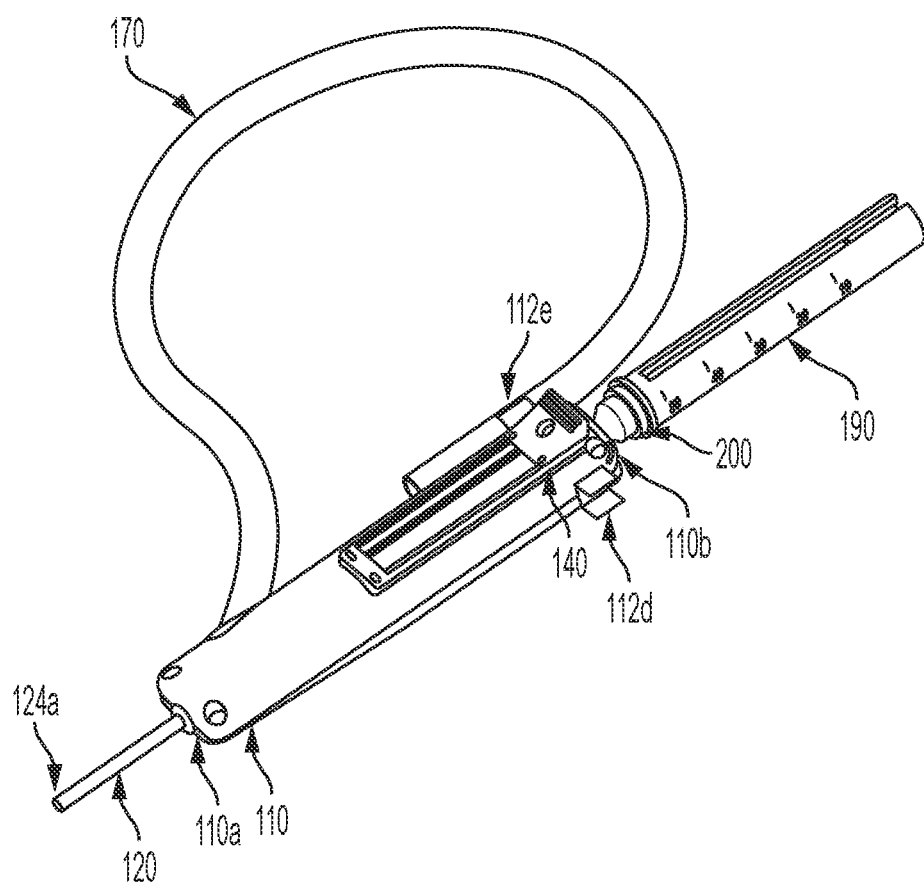
FIG. 2 is a front perspective view of the housing member of FIG. 1, with the needle member (not visible) retracted.
Figure 3:
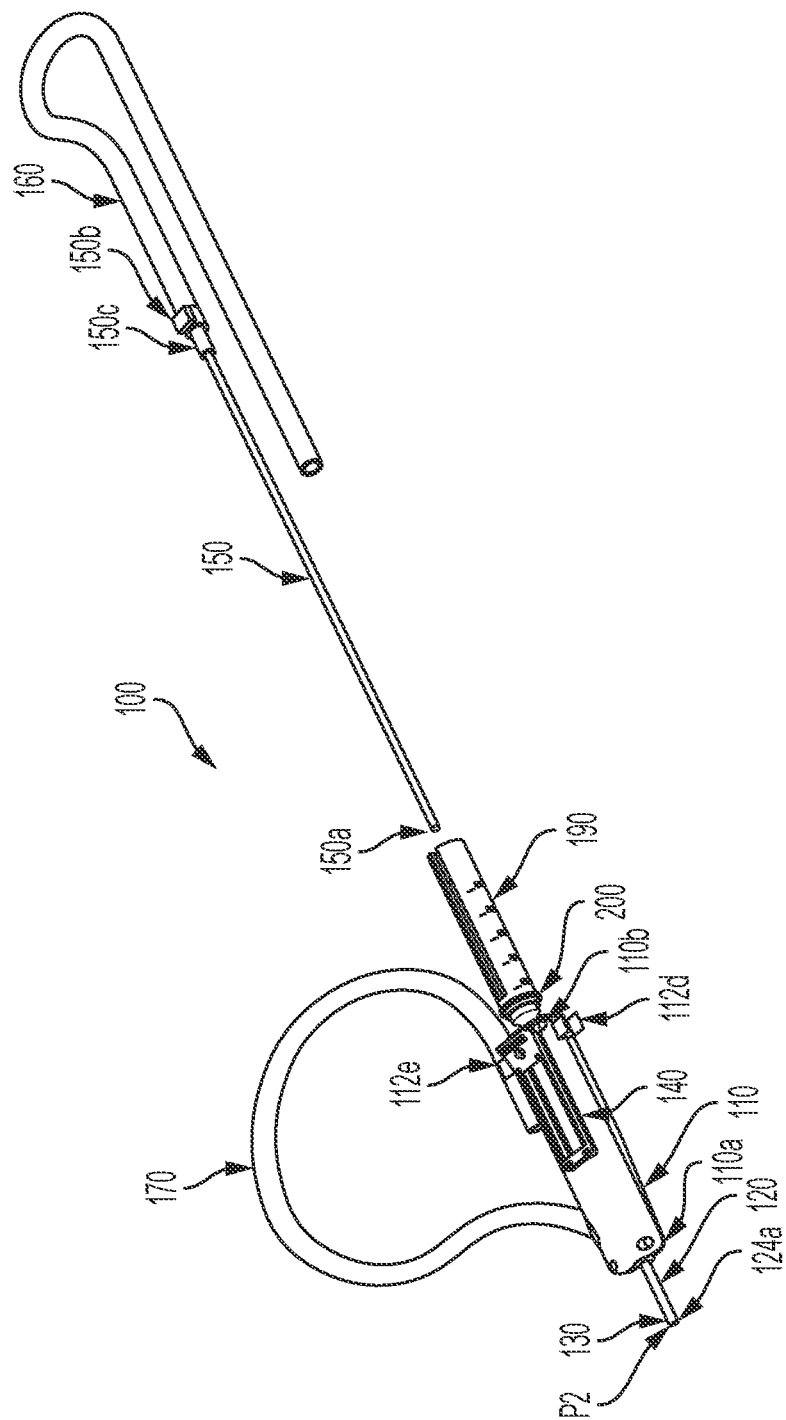
FIG. 3 is a front perspective view of the integrated catheter device of FIG. 1, showing the housing member with the needle member extended and the inner lumen member that cooperates with the housing member.
Figure 4:
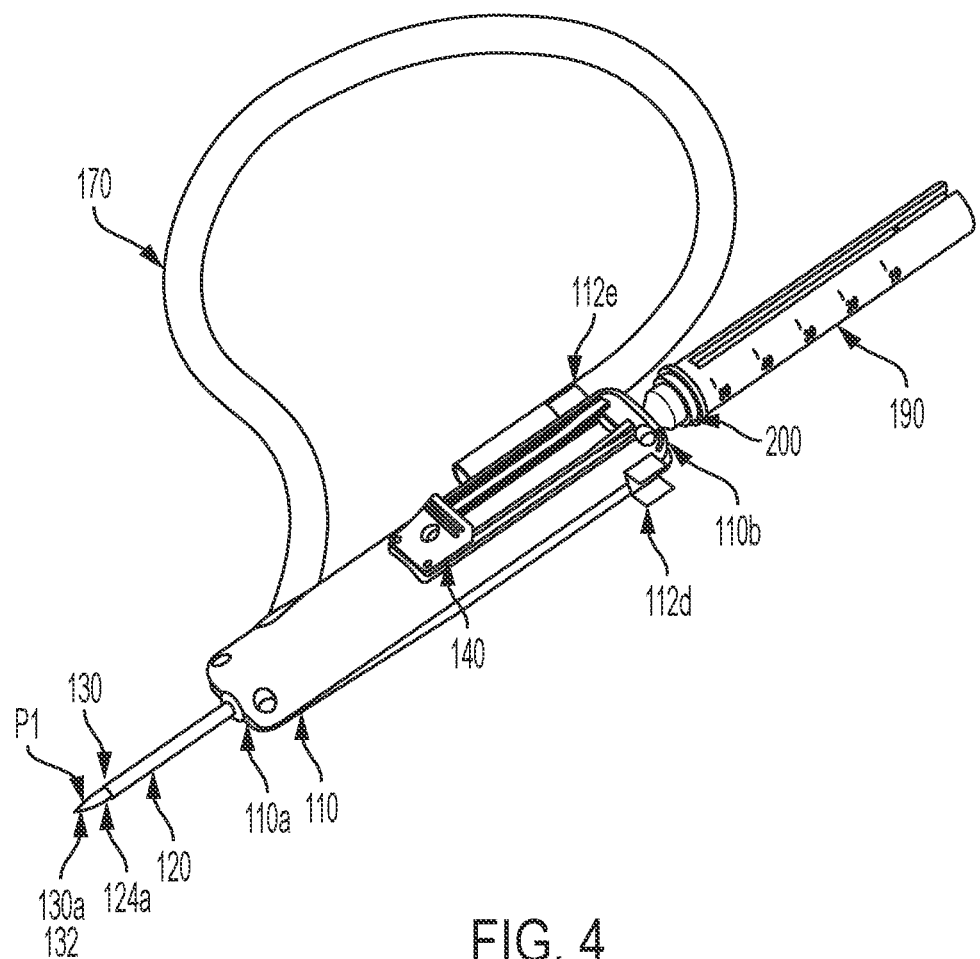
FIG. 4 is a front perspective view of the housing member of FIG. 1, with the needle member extended.

Reference will now be made in detail to the exemplary embodiments of the present general inventive concept, examples of which are illustrated in the accompanying drawings, wherein like reference numerals refer to the like elements throughout. The exemplary embodiments are described below in order to explain the present general inventive concept by referring to the figures. It is understood that the drawings provided herein are representations of exemplary embodiments of the present general inventive concept and are neither limiting nor drawn to scale.

Referring to FIGS. 1-6, in an example embodiment, an integrated catheter device 100 includes a housing member 110 having a first end 110a and an opposing second end 110b, an outer lumen member 120 designed to extend from the first end 110a of the housing member 110, and a needle member 130 (visible in FIGS. 3-6) slidably (or movably) coupled to the housing member 110. The integrated catheter device 100 further includes an inner lumen member 150 disposable through the housing member 110 and outer lumen member 120 (e.g., the inner lumen member 150 has an outer diameter smaller than an inner diameter of the outer lumen member 120). The housing member 110 includes a coupling body member 200 at the second end 110b of the housing member 110 by which the inner lumen member 150 can be coupled to the housing member 110 to secure the inner lumen member 150 relative to the outer lumen member 120. Preferably, the coupling body member 200 is a luer lock.

Figure 5:
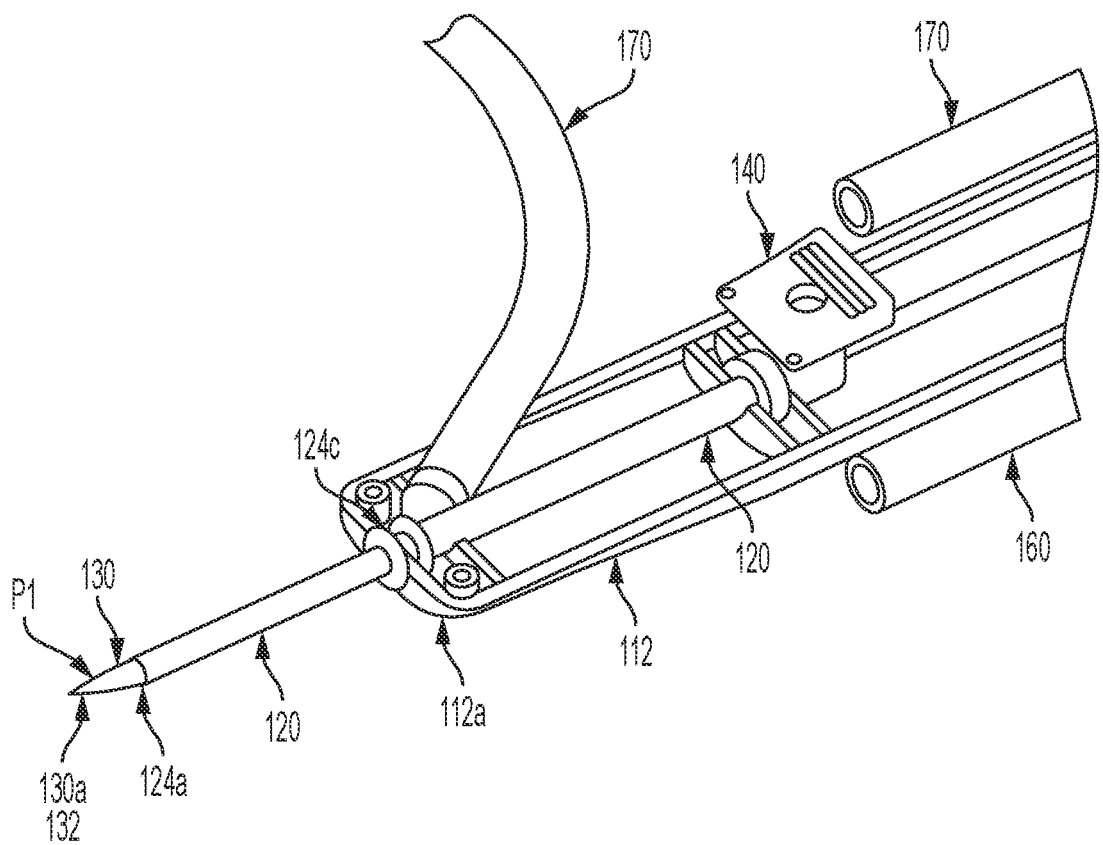
FIG. 5 is a front perspective view of the housing member of FIG. 1, with a housing cover removed and the needle member retracted.
Figure 6:
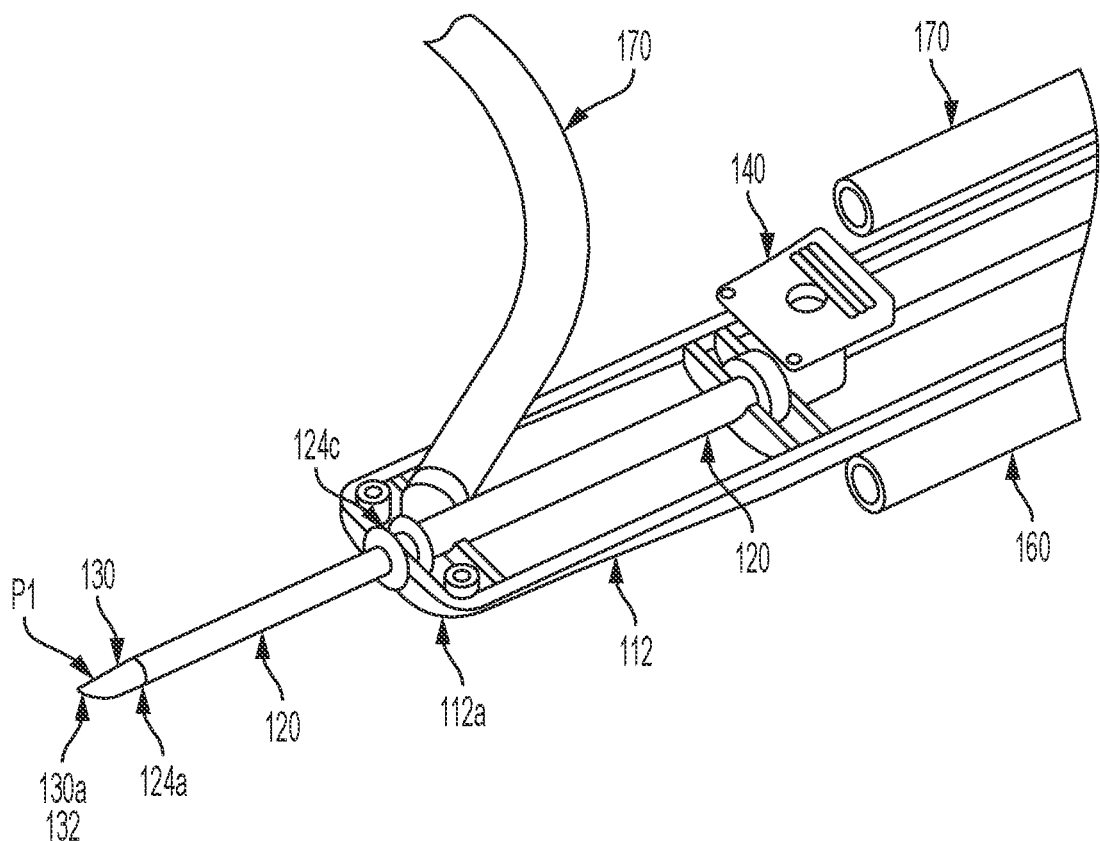
FIG. 6 is a front perspective view of the housing member of FIG. 1, with a housing cover removed and the needle member extended.
Figure 7A:
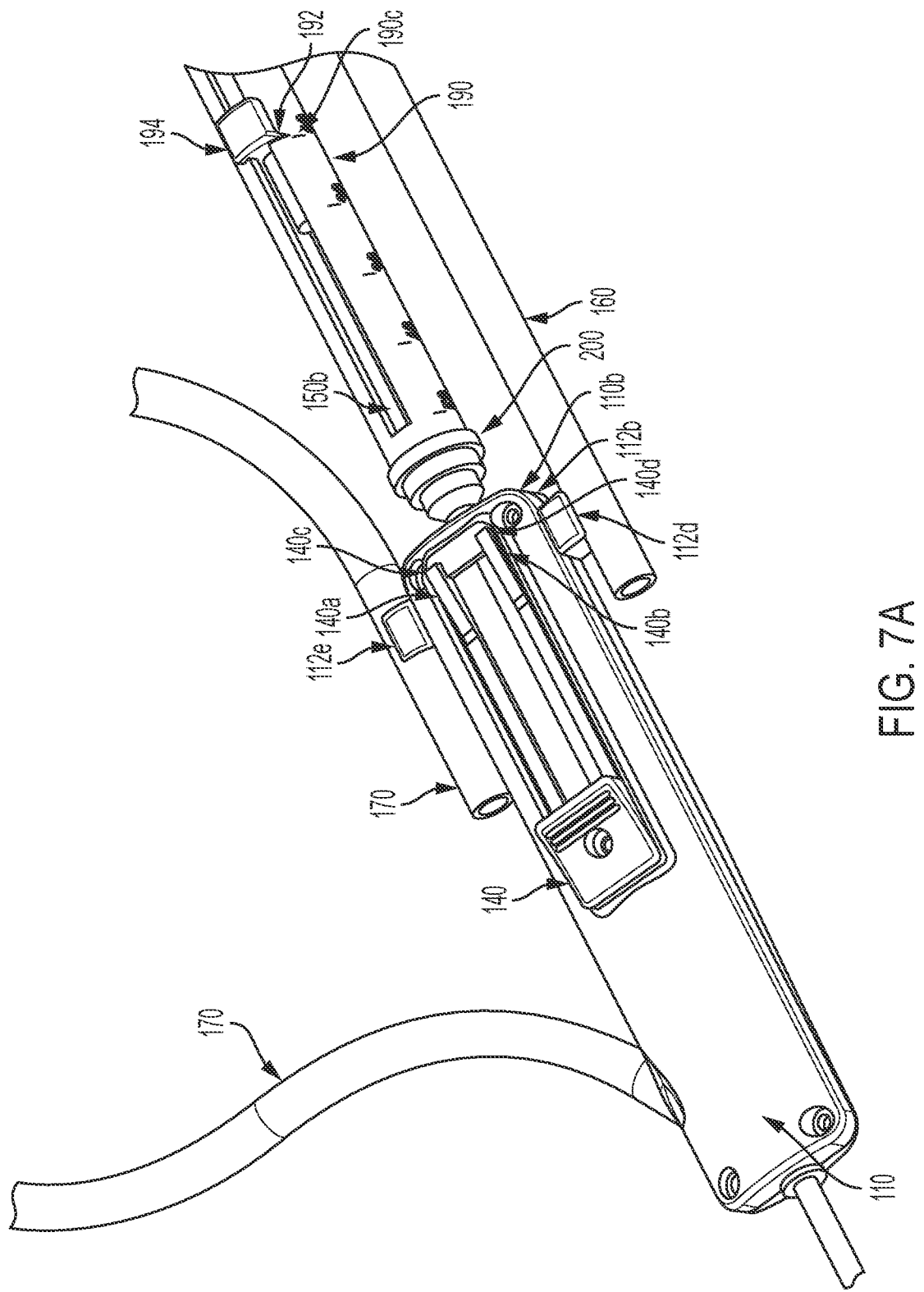
FIGS. 7A and 7B illustrate locking slide button features of an integrated catheter device according to an example of the present general inventive concept.
Figure 7B:
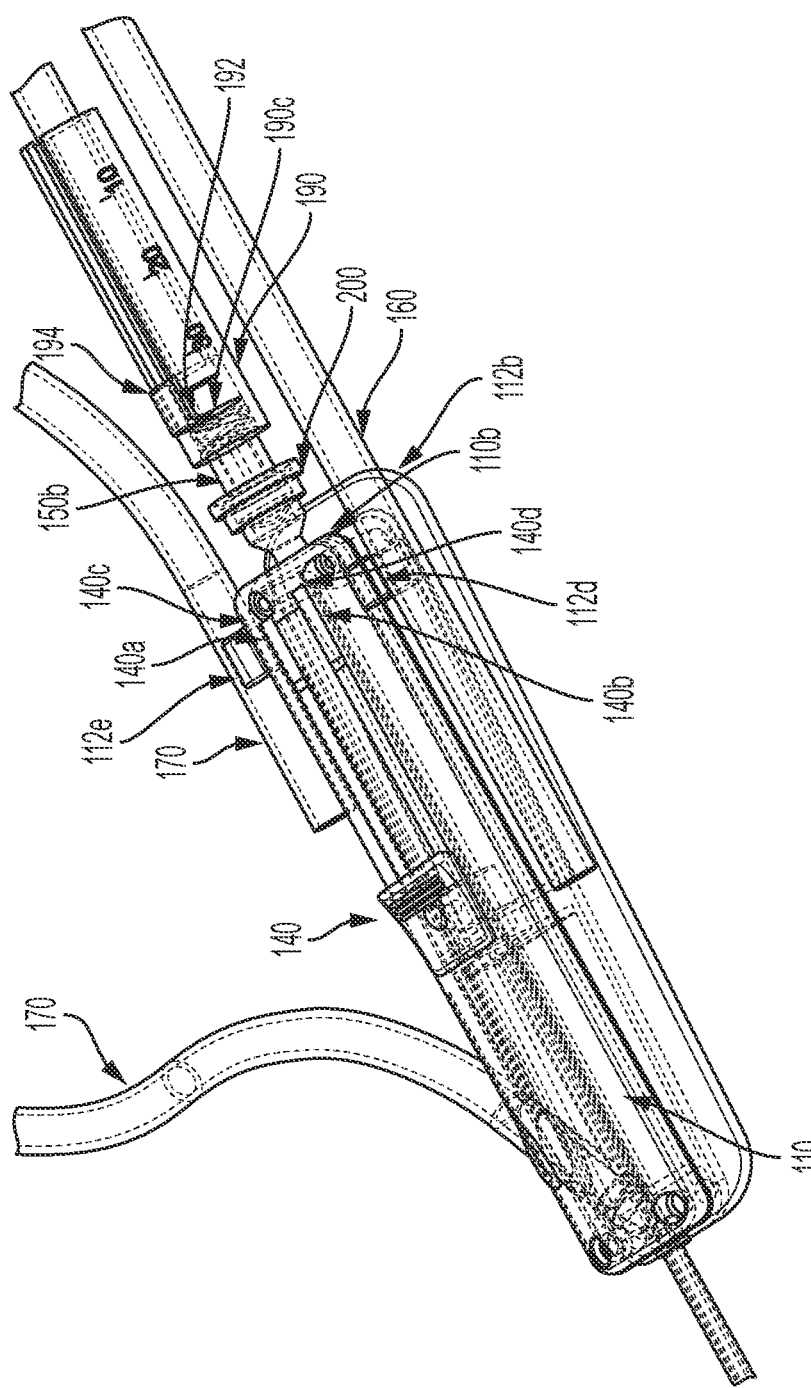
Figure 8A:
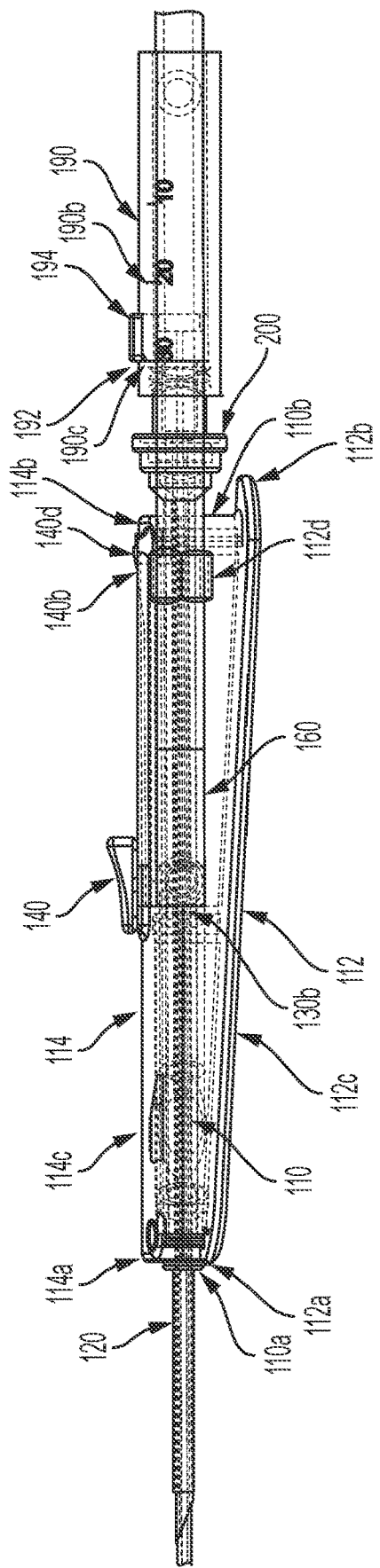
FIGS. 8A, 8B, and 8C illustrate non-parallel outer surfaces of a housing member of an integrated catheter device according to an example of the present general inventive concept.
Figure 8B:
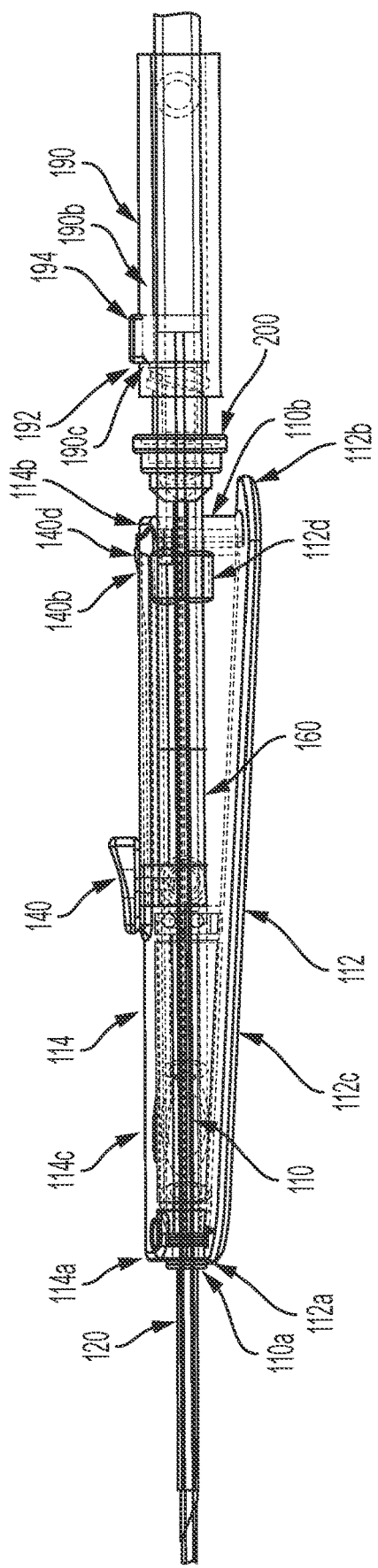
Figure 8C:
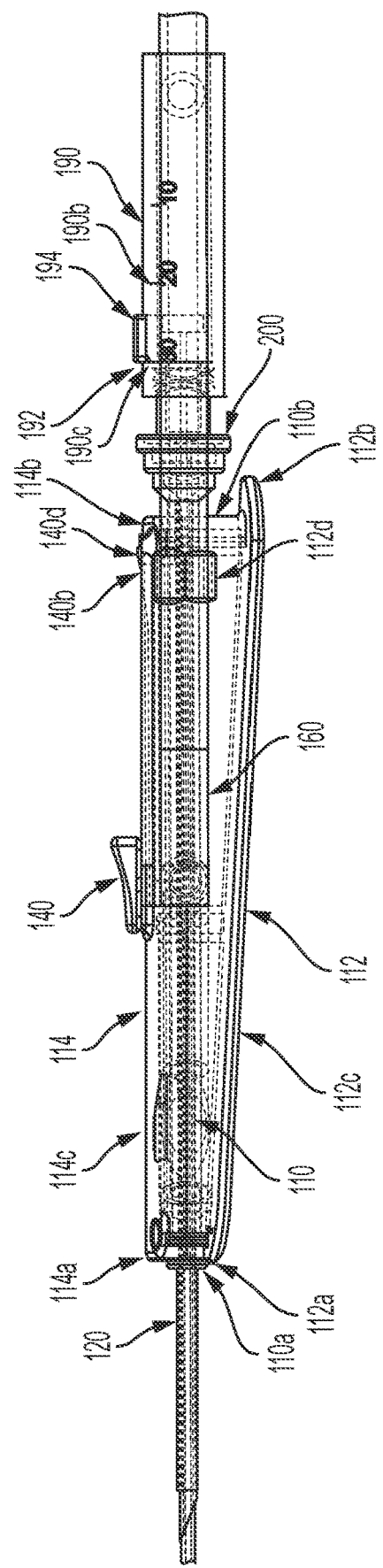
Figure 9:
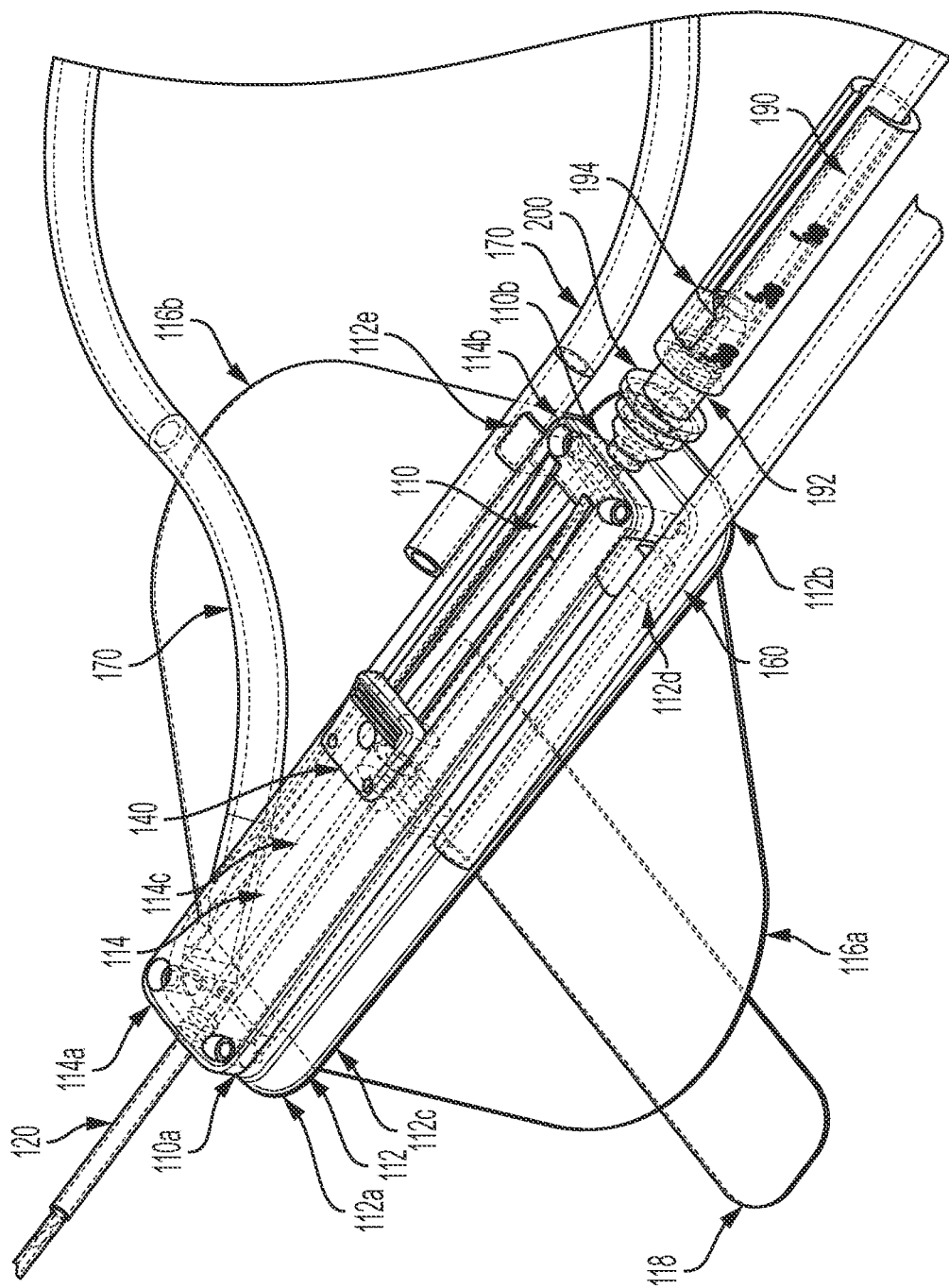
FIG. 9 illustrates attachment features of a housing member of an integrated catheter device according to an example of the present general inventive concept.

Referring now also to FIGS. 7-9, in the present embodiment, the housing member 110 includes a base member 112 (best visible in FIGS. 5 and 6) and a cover member 114 (visible in FIGS. 1-4) which is assembled onto the base member 112 to slidably (or movably) support the needle member 130 (visible in FIGS. 3-6). The base member 112 has a first end 112a and an opposing second end 112b (best visible in FIGS. 7-9).

Referring again to FIG. 8, preferably, the housing member 110 is configured with an outer surface 112c of the base member 112 non-parallel to an outer surface 114c of the cover member 114 so as to configure the second end 110b of the housing member 110 to be taller than the first end 110a of the housing member 110, such that when the housing member 110 is held adjacent a target area of a patient, longitudinal axes of the outer lumen member 120 and inner lumen member 150 are angled with respect to the target area (e.g., angled toward the target area) to, among other benefits, (1) facilitate insertion of the needle member 130 into an arteriovenous fistula of the patient, as described more fully below, and (2) facilitate easier access to and visibility of the housing member 110 and its features by users.

Referring again to FIG. 9, further preferably, the housing member 110 includes one or more attachment features, such as, for example, one or more extending flaps 116a,116b and/or one or more adhesive strips 118, that are configured to facilitate attachment of the housing member 110, and most preferably the base member 112, to the skin of the target area of the patient. Preferably, the flaps 116a,116b are contoured to approximate a curvature of a patient's arm.

Referring again to FIGS. 1-4 and 7-9, further preferably, the housing member 110 includes one or more tube management features, such as, for example, one or more channels 112d,112e into which a tube of the device 110 (e.g., inflow tube 160 and outflow tube 170 as discussed below) can be snapped or by which can otherwise releasably be held adjacent the housing member 110. Preferably, when the tube is held in the channel 112d,112e, the tube is permitted to slide relative to the tube along a longitudinal axis of the channel 112d,112e.

In the present embodiment, the outer lumen member 120 is manufactured from a flexible material and extends from the first end 112a of the base member 112. Preferably, the flexible material is Pebax or PebaSlix. However, the present general inventive concept is not limited thereto.

In the present embodiment, as best visible in FIGS. 5 and 6, the needle member 130 is coupled to a slide button 140 that is configured to assist a user to move the needle member 130 from a first position P1 to a second position P2. The needle member 130 extends beyond the outer lumen member 120 when the slide button 140 is moved toward the first end 110a of the housing member 110 to place the needle member 130 into the first position P1. Conversely, the needle member 130 is concealed within the outer lumen member 120 when the slide button 140 is moved toward the second end 110b of the housing member 110 to place the needle member 130 into the second position P2. Preferably, the slide button 140 can be locked in each position. For example, as illustrated in FIGS. 7 and 8, a slide surface of the cover member 114 with which the slide button 140 cooperates can be configured with ramps 140a,140b and walls 140c,140d to prevent reverse movement of the slide button 140 when placed in each position.

Preferably, as best visible in FIGS. 5 and 6, the outer lumen member 120 includes a plurality of ports in including a first port 124a disposed at a first end 120a of the outer lumen member 120, a second port 124b disposed at a second end 120b of the outer lumen member 120, and a third port 124c disposed between the first port 124a and the second port 124b.

Further preferably, as best visible in FIGS. 5 and 6, the needle member 130 includes a first tip 132 at a first end 130a of the needle member 130 and a second tip 134 at an opposing second end 130b of the needle member 130. In the present embodiment, the first tip 132 of the needle member 130 is formed as a sharp tip and the second tip 134 is formed as a blunt tip. Preferably, the needle member 130 is hollow to permit blood flow and has a relief port 136 disposed between the first tip 132 and the second tip 134, and the relief port 136 aligns with the third port 124c of the outer lumen member 120 when the needle member 130 is at the first position P1, such that blood flowing into the needle member 130 is diverted.

The needle member 130 preferably is sized inclusively between 17 G and 14 G and supports blood flow rates inclusively between 200 and over 450 cc per minute. More specifically, for blood flow rates less than 300 cc/min, the recommended needle gauge is 17 G; for blood flow rates 300 cc/min to 350 cc/min, the recommended needle gauge is 16 G; for blood flow rates over 350 cc/min up to 450 cc/min, the recommended needle gauge is 15 G; and for blood flow rates over 450 cc/min, the recommended needle gauge is 14 G.

Figure 10A:
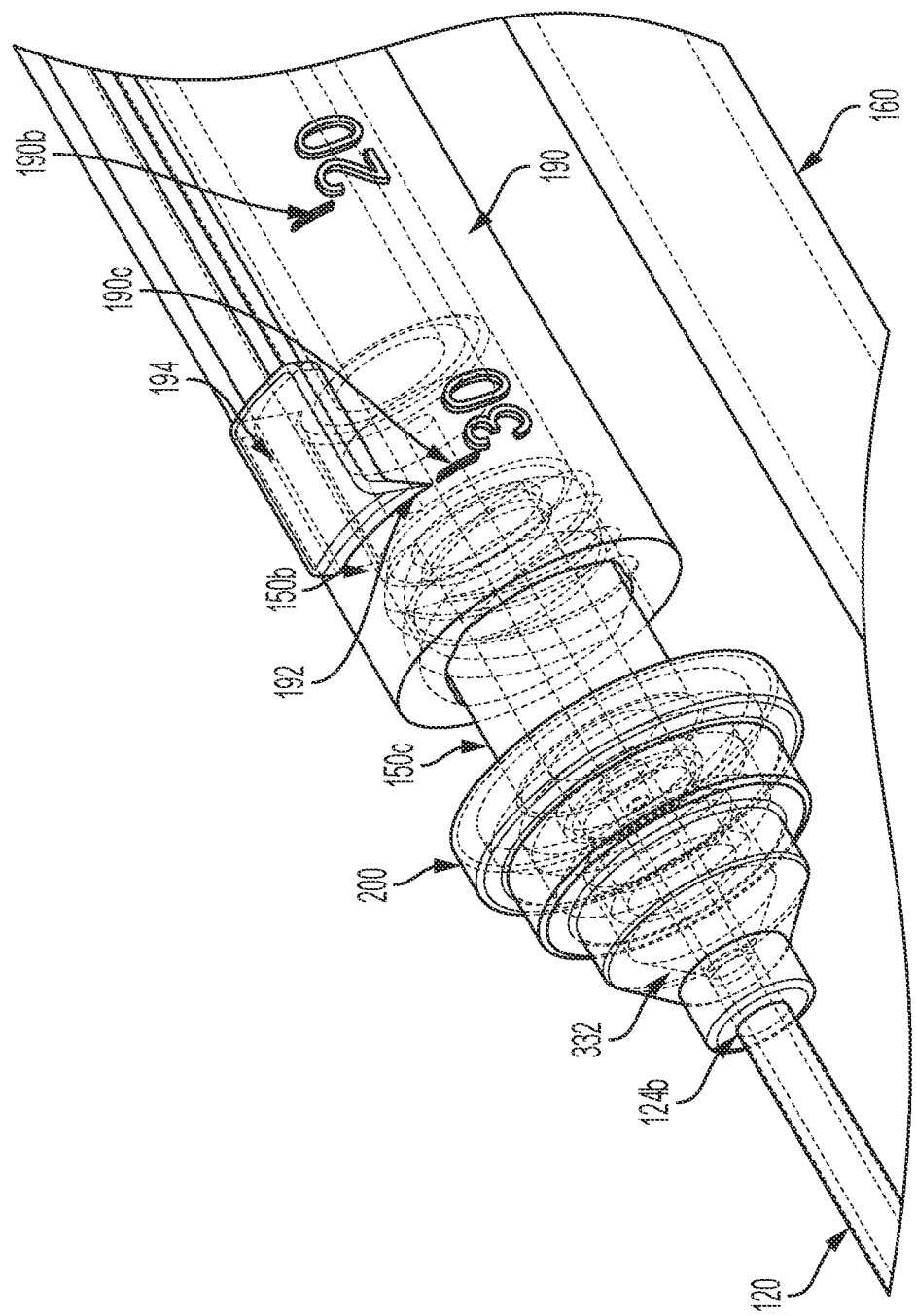
FIGS. 10A and 10B illustrate an end flash feature of an integrated catheter device according to an example of the present general inventive concept.
Figure 10B:
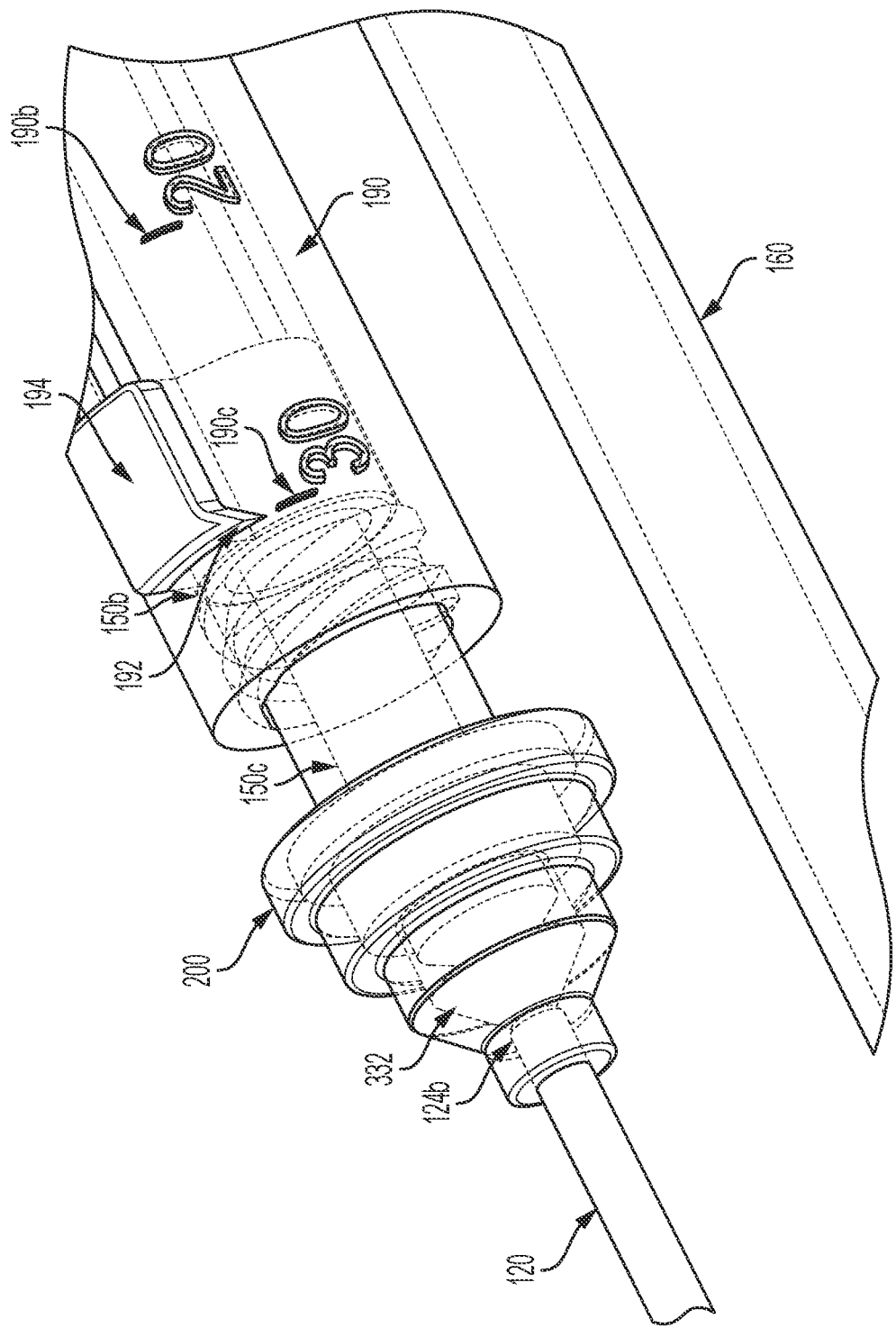

Further preferably, as best shown in FIGS. 5 and 6, the first tip 132 of the needle member 130 can be extended from and retracted into the first port 124a of the outer lumen member 120 by operation of the slide button 140. As will be described further below, when the needle member 130 is extended, and the first tip 132 of the needle member 130 is inserted into an arteriovenous fistula of a patient, a flash of blood 330 from the arteriovenous fistula enters the needle member 130 and is diverted by the relief port 136 to the third port 124c of the outer lumen member 120 due to the alignment of the relief port 136a and the third port 124c. Preferably, the flash of blood 330 is visible adjacent the third port 124c as an indication that the vein has been accessed. In preferred embodiments, alternatively or additionally, as illustrated in FIG. 10, the flash of blood 332 is visible adjacent the second port 124b as an indication that the arteriovenous fistula has been accessed.

Referring again to FIGS. 1-3 and also to FIGS. 7-12, the inner lumen member 150 preferably has a first end 150a that is dimensioned to pass into the second port 124b of the outer lumen member 120, through the outer lumen member 120, and out from the first port 124a of the outer lumen member 120. Preferably, the inner lumen member 150 has a diameter which in such a configuration permits blood from the arteriovenous fistula to flow between an outer wall of the inner lumen member 150 and an inner wall of the outer lumen member 120 and out the third port 124c of the outer lumen member 120.

Figure 16:
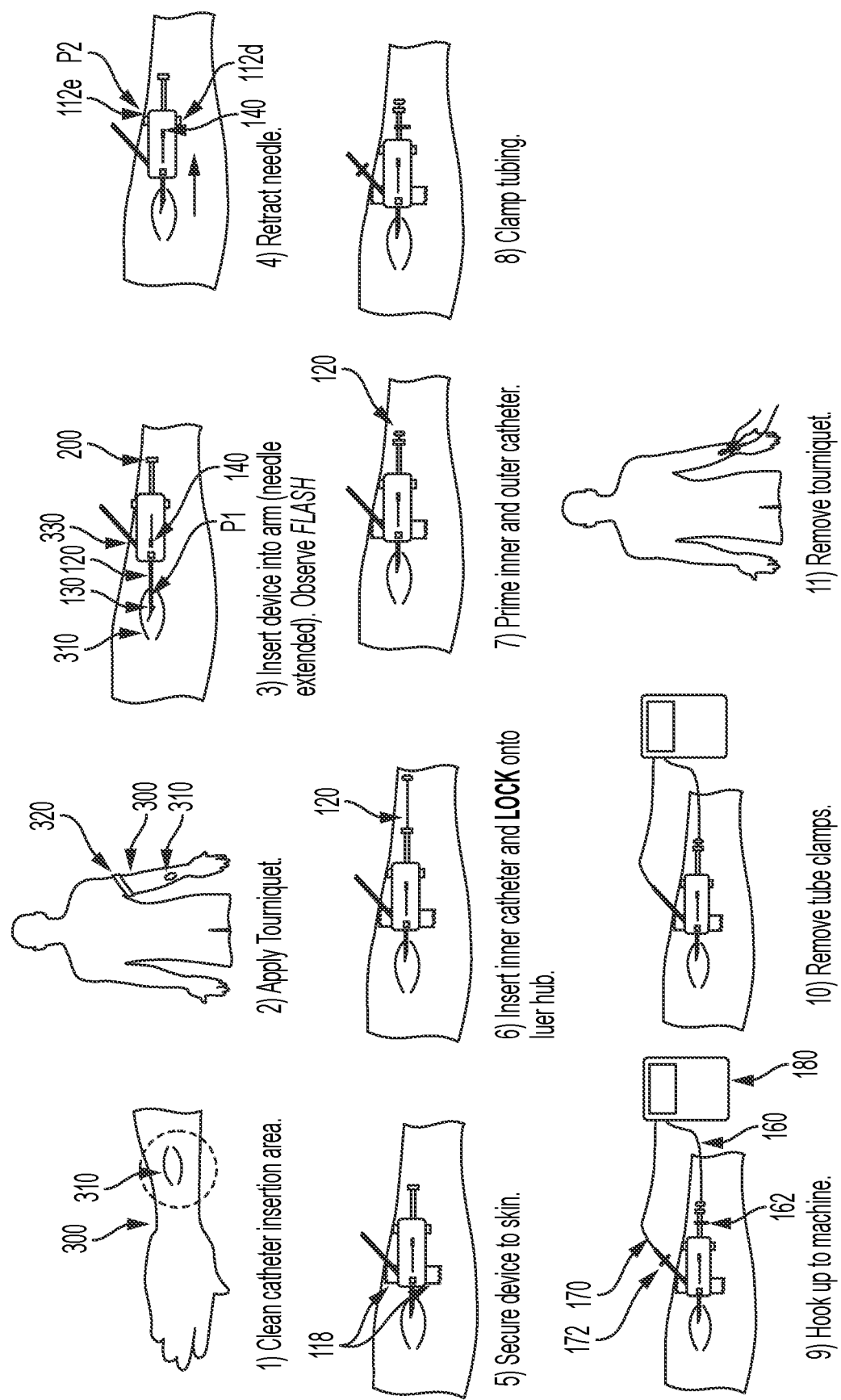
FIG. 16 illustrates use of an integrated catheter device according to an example of the present general inventive concept.

Referring also to FIG. 16, the inner lumen member 150 preferably has a second end 150b that is connected to an inflow tube 160 that can be connected to a dialysis machine 180, as described further below. Accordingly, dialyzed blood from the machine 180 can be introduced into and through the inner lumen member 150.

Figure 11:
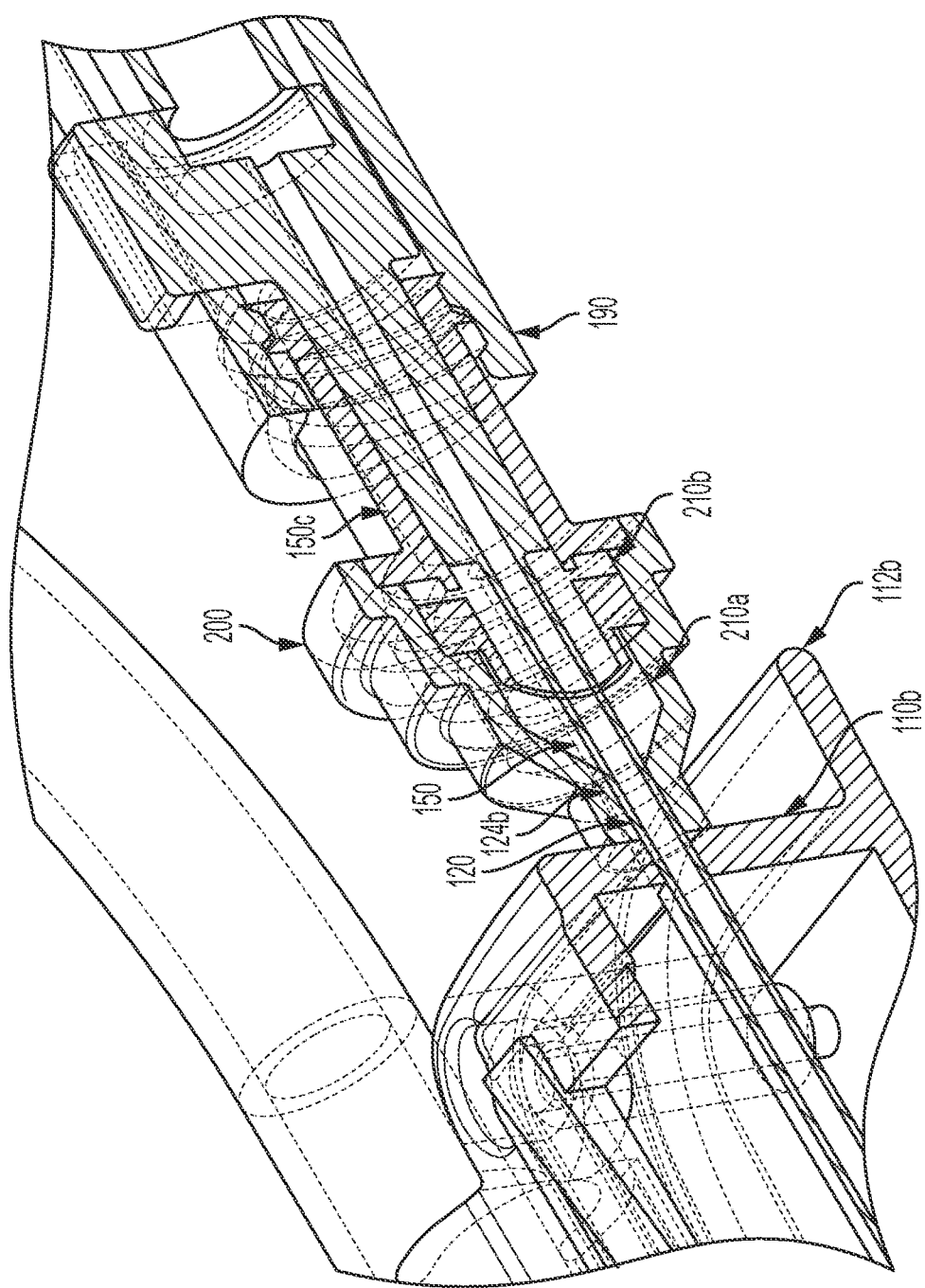
FIG. 11 illustrates inner lumen sealing features of an integrated catheter device according to an example of the present general inventive concept.
Figure 12:
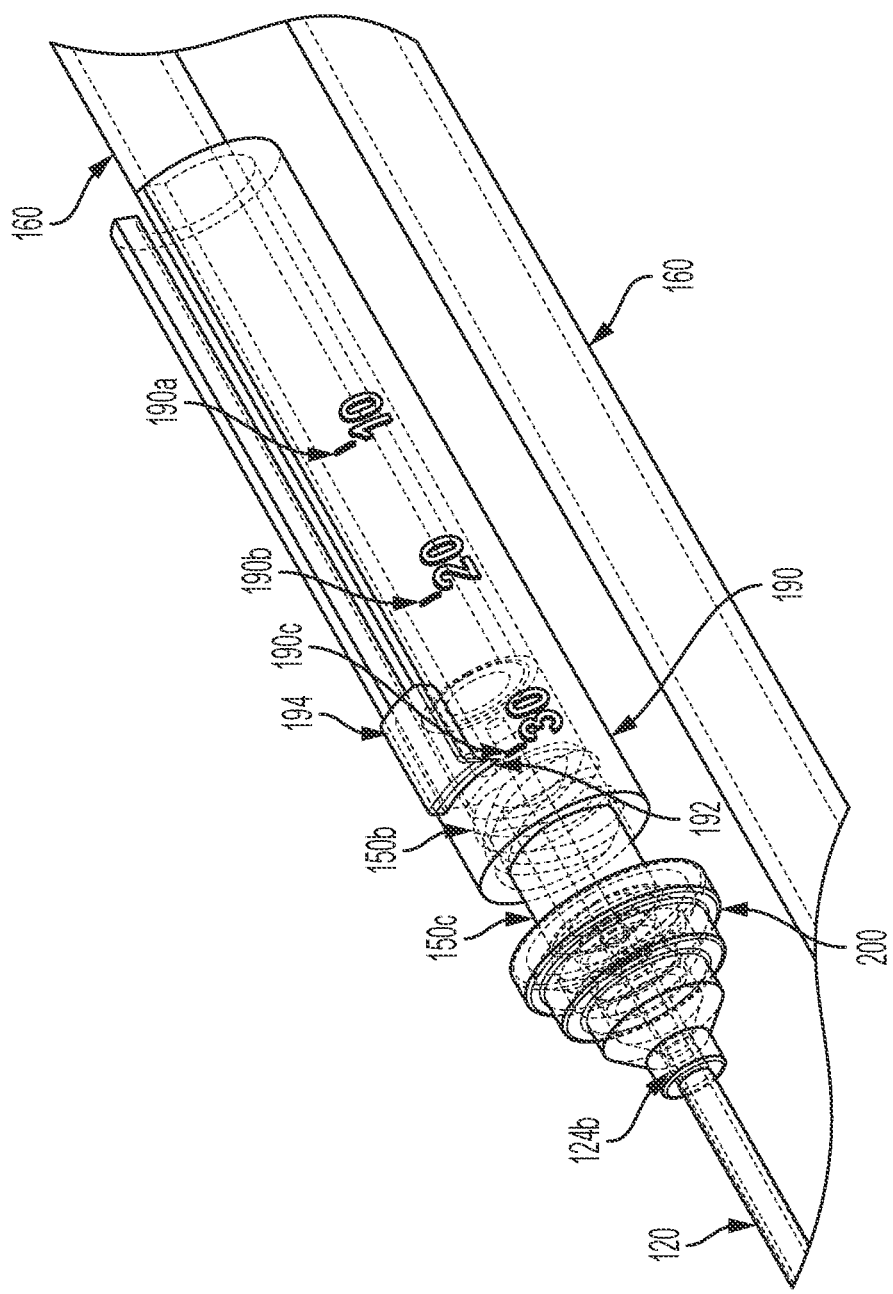
FIG. 12 illustrates depth gauge features of an integrated catheter device according to an example of the present general inventive concept.
Figure 13:
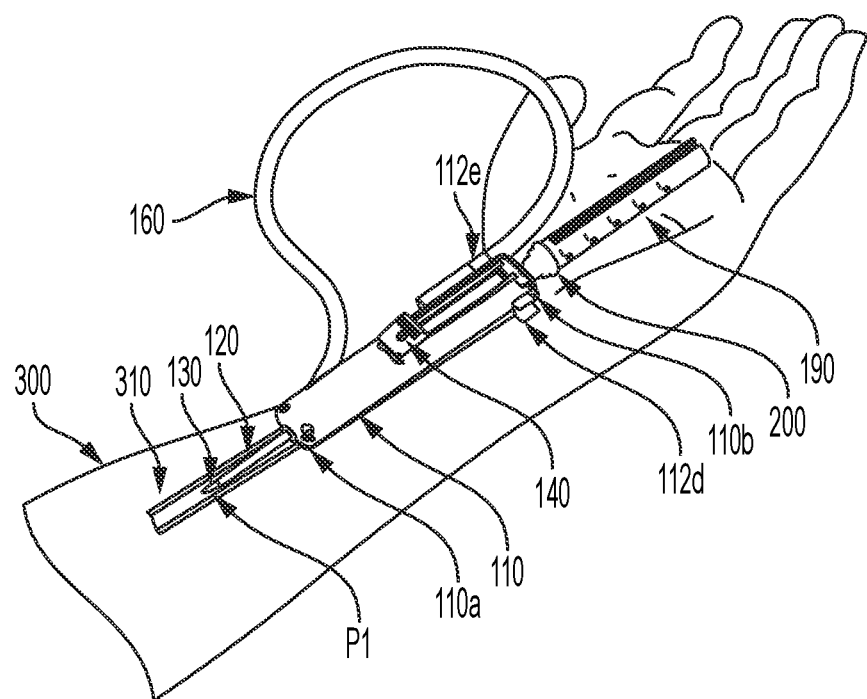
FIG. 13 is a front perspective view of the housing member in the configuration of FIG. 6, with the needle member inserted into a vein of a patient.
Figure 14:
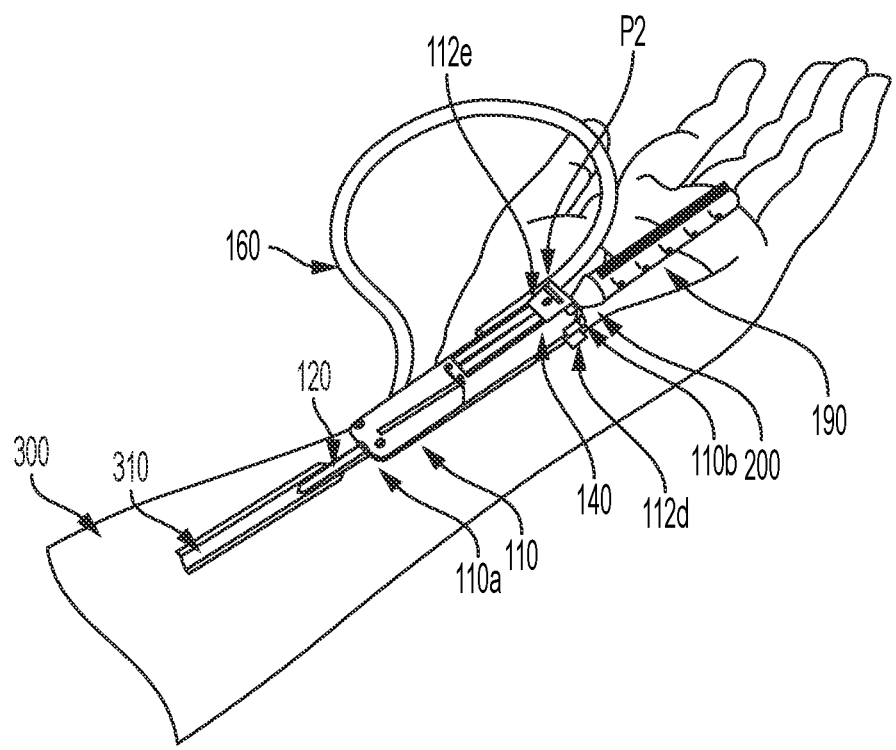
FIG. 14 is a front perspective view of the housing member in the configuration of FIG. 5, with the needle member retracted into the outer lumen.
Figure 15:
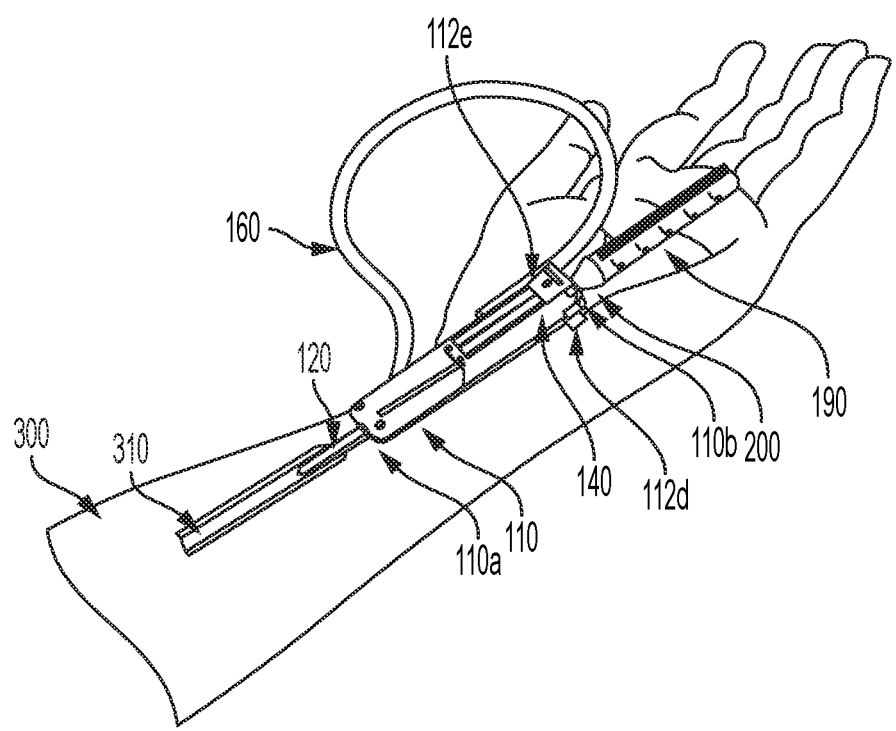
FIG. 15. is a front perspective view of the housing member in the configuration of FIG. 5, with the inner lumen member inserted into an arteriovenous fistula of a patient.

The inner lumen member 150 preferably has a locking portion 150c that can be secured to the coupling body member 200 at the second end 110b of the housing member 110. Preferably, when the locking portion 150c is secured to the coupling body member 200, the inner lumen member 150 is fixed relative to the outer lumen member 120 and the second port 124b of the outer lumen member 120 is sealed to prevent outflow of blood. Preferably, as illustrated in FIG. 11, the coupling body member 200 includes sealing features 210a,210b that cooperate with the locking portion 150c of the inner lumen member 150 to accomplish such outflow prevention.

Preferably, as best shown in FIGS. 7-10 and 12, the integrated catheter device 100 further includes a depth gauge 190 that cooperates with a depth marker 192 on the inner lumen member 150 in a configuration in which the depth marker 192 indicates a distance from which a first end 150a of the inner lumen member 150 extends past the first port 124a of the outer lumen member 120 when the inner lumen member 150 is pass into the second port 124b of the outer lumen member 120, through the outer lumen member 120, and out from the first port 124a of the outer lumen member 120. For example, the depth gauge 190 preferably includes markings 190a, 190b, 190c at 10 mm, 20 mm and 30 mm distances, respectively, along its length, and the depth marker 192 aligns with one of the markings when positioned at a corresponding depth distance.

Further preferably, as best shown in FIGS. 7-10 and 12, the integrated catheter device 100 includes a depth slider 194 configured to facilitate moving the first end 150a of the inner lumen member 150 forward outwardly from and backward inwardly toward the first end 124a of the outer lumen member 120. Preferably, the depth slider 194 is configured to be operable by a thumb of a user. Further preferably, the depth slider 194 is integrated with the depth marker 192 discussed above.

With regard to use of the integrated catheter device 100, and with reference also to FIGS. 13-16, a target area 310 of an arm 300 of a patient is prepared. For example, skin of the target area 310 of the arm 300 is sterilized (see, e.g., FIG. 16, Step 1), and a tourniquet 320 is applied to the arm between a shoulder of the patient and the target area 310 (see, e.g., FIG. 16, Step 2). Alternative preparations of the target area 310 in anticipation of use of the integrated catheter device 100 are also contemplated, and preferred preparations are those determined by a qualified physician.

Once the target area 310 is prepared, the needle member 130 is extended by being placed in the first position P1 by moving the slide button 140 toward the first position P1. When the needle member 130 is in the first position P1, the first tip 132 of the first end 130a of the needle member 130 is extended from the outer lumen member 120.

With the first tip 132 of the first end 130a of the needle member 130 extended from the outer lumen member 120, the first tip 132 is pressed against the target area 310 to break the skin and continued pressing causes the first tip 132 and the outer lumen member 120 to enter an arteriovenous fistula of the patient and remain there. When the first tip 132 enters the arteriovenous fistula, a flash of blood 330 flows into the needle member 130, out the relief port 136 of the needle member 130 and toward the third port 124c of the outer lumen member 120, where it is observed. (See, e.g., FIG. 13 and FIG. 16, Step 3.)

Once the flash of blood is observed, the needle member 130 is retracted by being placed in the second position P2 by moving the slide button 140 toward the second position P2 (see, e.g., FIG. 16, Step 4).

Once the needle member 130 is retracted, the housing member 110 is secured to the target area 310 using one or more of the attachment features 116a, 116b, 118 of the housing member 110 (see, e.g., FIG. 16, Step 5).

Once the housing member 110 is secured to the target area 310, the inner lumen member 150 is inserted into and through the second port 124b of the outer lumen member 120 until the first end 150a of the inner lumen member 150 extends from the outer lumen member 120 into the arteriovenous fistula. The locking portion 150c of the inner lumen member 150 is then locked to the coupling body member 200 (e.g., the luer lock) of the housing member 110. (See, e.g., FIG. 16, Step 6.)

Once the inner lumen member 150 is locked to the coupling body member 200, the inner lumen member 150 and outer lumen member 120 are primed to effect blood flow (see, e.g., FIG. 16, Step 7), a tube 160 attached to the inner lumen member 150 is clamped (e.g., with an inner lumen tube clamp 162) to temporarily prevent blood flood from the arteriovenous fistula, and an outflow tube 170 of the outer lumen member 120 is clamped (e.g., with an outer lumen tube clamp 172) to temporarily prevent blood flood into the arteriovenous fistula (see, e.g., FIG. 16, Step 8).

Once the tubes 160, 170 are clamped, the tubes 160, 170 are connected to a dialysis machine 180, with the tube 160 connected to the inner lumen 150 configured to pass blood from the machine 180, and the tube 170 connected to the outer lumen 120 configured to pass blood to the machine 180 (see, e.g., FIG. 16, Step 9). The tubes 160, 170 are then unclamped to permit blood flow accordingly (see, e.g., FIG. 16, Step 10), and the tourniquet 320 is removed (see, e.g., FIG. 16, Step 11). The blood replacement process then continues for a desired or recommended amount of time.

Once the blood replacement process has continued for the desired or recommended amount of time, the machine 180 is deactivated, the tubes 160,180 are clamped and then disconnected from the machine. Then, the locking portion 150c of the inner lumen member 150 is unlocked from the coupling body member 200 of the housing member 110, and the inner lumen member 150 is removed from the outer lumen member 120. Then, the housing member 110 is removed from the target area 310 of the patient, and the outer lumen member 120 is removed from the arteriovenous fistula of the patient. Finally, the wound is sterilized and bandaged.

Referring now to FIGS. 17-26, an alternate embodiment of the present invention is shown. Numerals in these figures usually correspond to similar elements in the preferred embodiment but with a 1000 series prefix. However, all element numbers in the alternate embodiments may not have a corresponding element in the preferred embodiment. Thus, all element numbers in the alternate embodiment may not follow the 1000 prefix convention mentioned above.

Figure 17A:
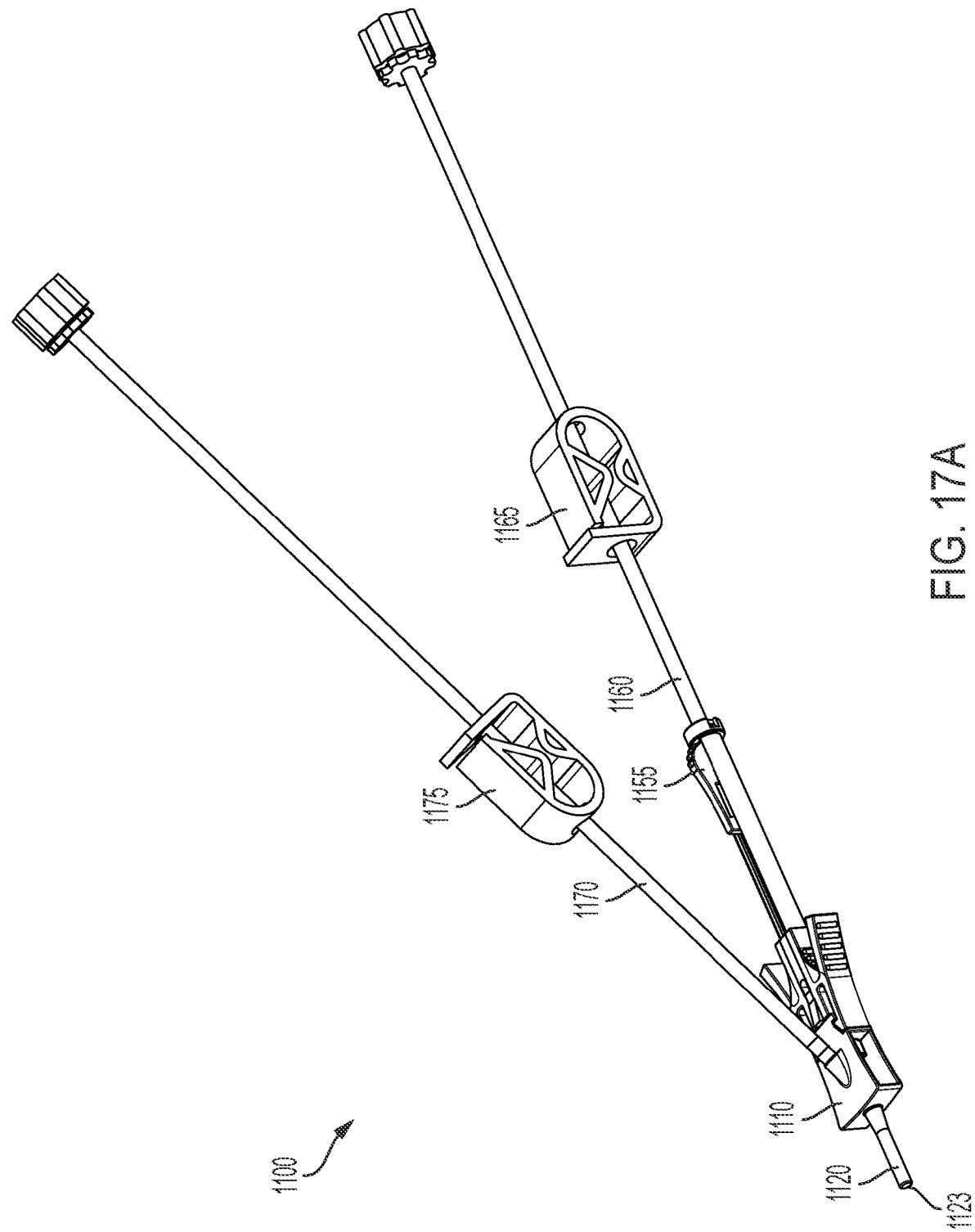
FIGS. 17A and 17B are perspective views of an alternate embodiment of the integrated catheter assembly.

Referring now to FIGS. 17A/B-19A/B, integrated catheter device 1100 includes a hub or housing member 1110 having a first end 1110a and an opposing second end 1110b. An outer lumen member 1120 extends from the first end 1110a of housing 1110. Outer lumen 1120 may be integrally molded as a part of the housing 1110. Housing 1110 and outer lumen 1120 define an open passageway 1901 extending therethrough.

Figure 17B:
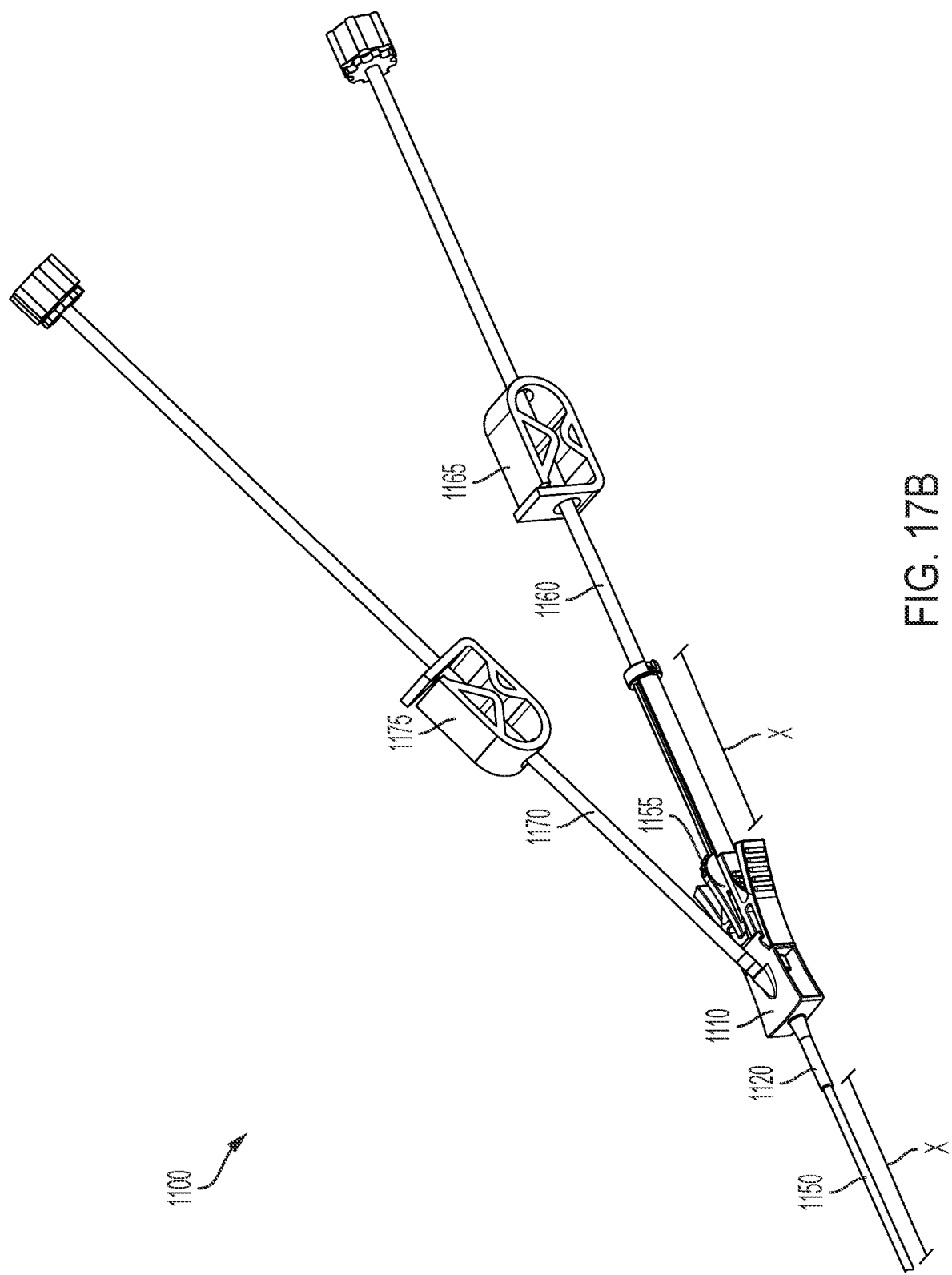

FIG. 17A is a perspective view of the alternate embodiment with inner lumen 1150 retracted within elongated member 1204 while FIG. 17B is a perspective view with inner lumen 1150 extended past outer lumen 1120 as discussed further below.

Figure 18:
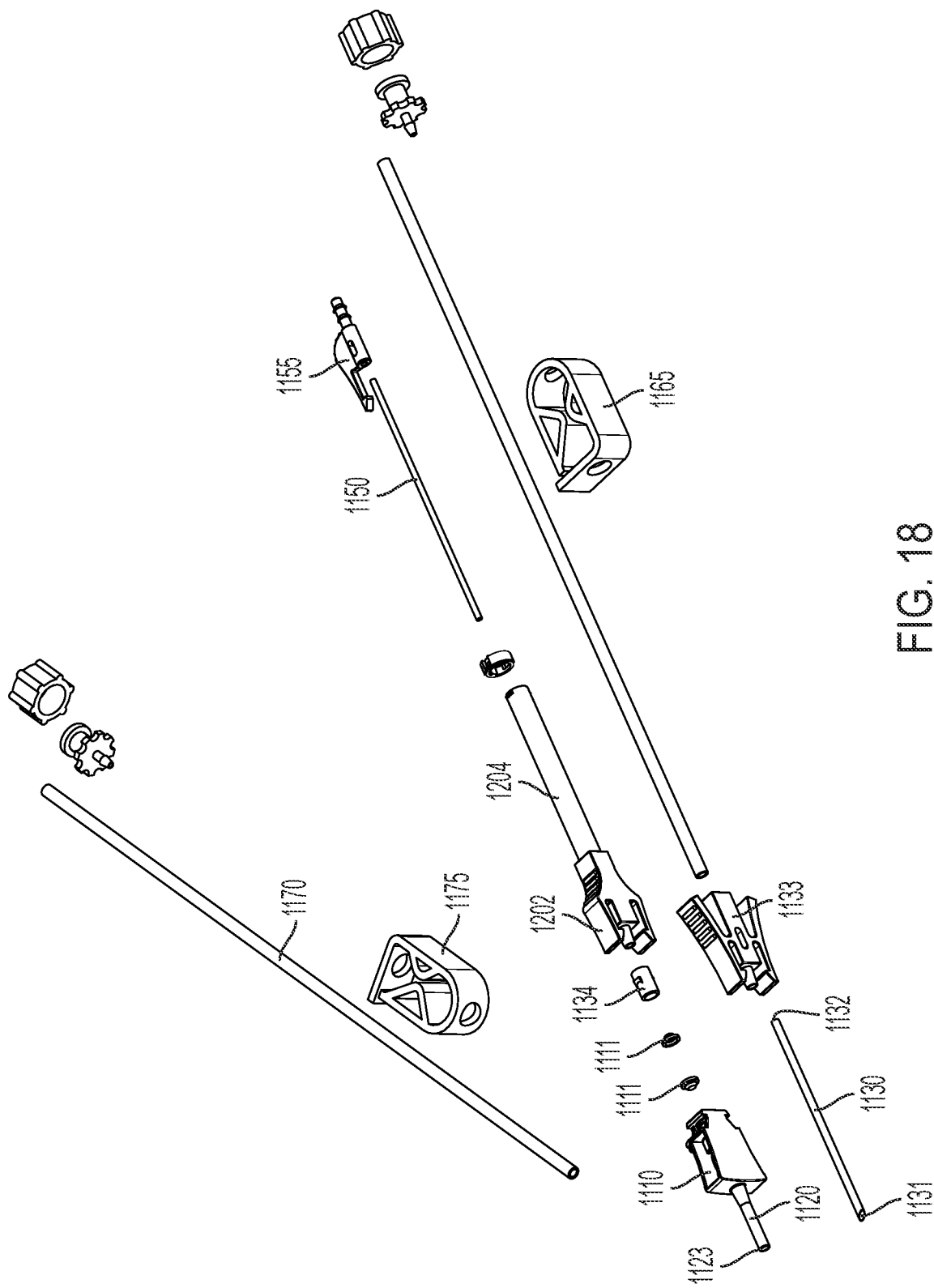
FIG. 18 is an exploded perspective view of the alternate embodiment generally shown in FIGS. 17A and 17B.
Figure 19A:
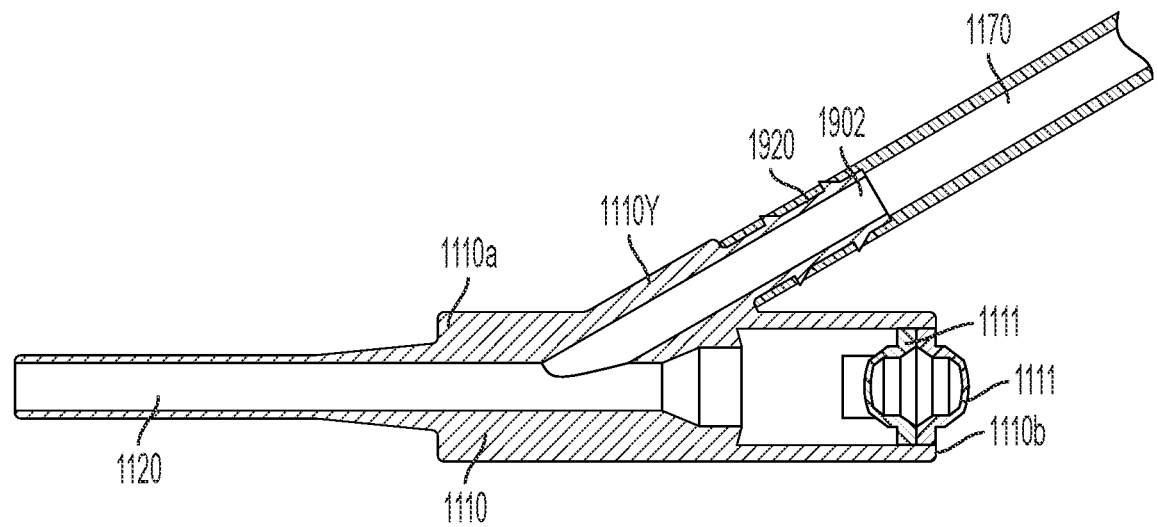
FIGS. 19A and 19B are cross sectional detail views of a hub and outer lumen of the alternate embodiment shown in FIGS. 17A/B and 18.
Figure 19B:
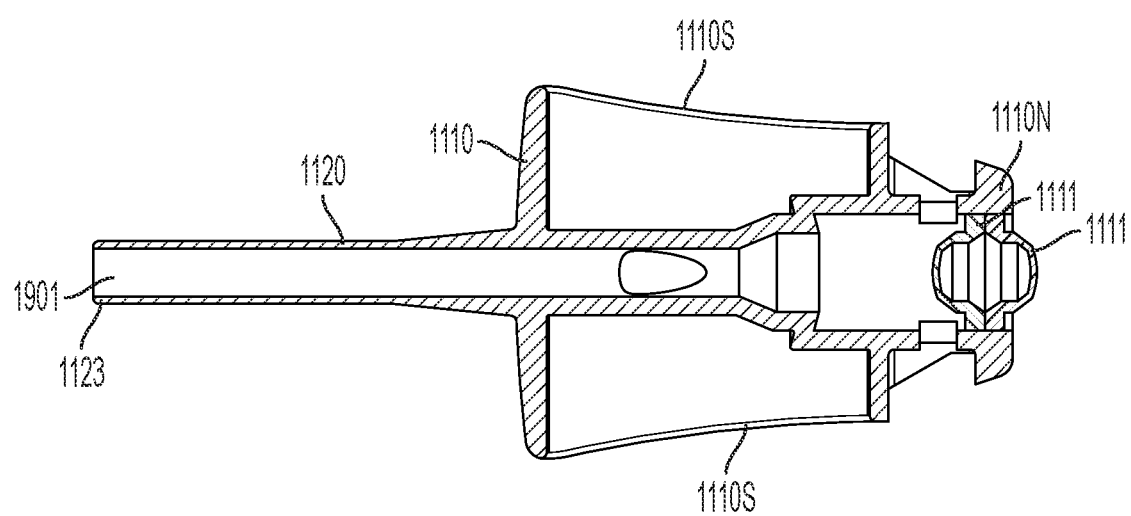
Figure 20:
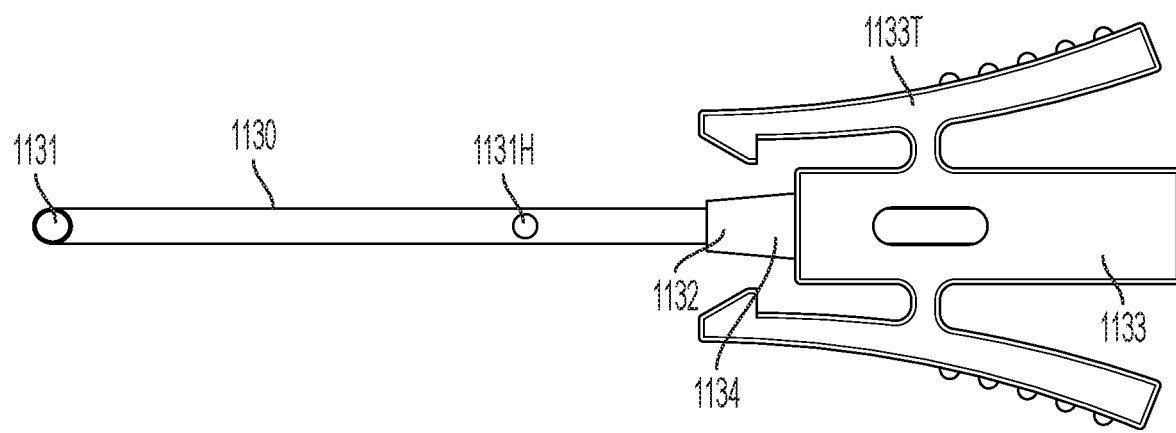
FIG. 20 is a detail view of a needle holder and a needle of the alternate embodiment as shown in FIGS. 17A/B.
Figure 21:
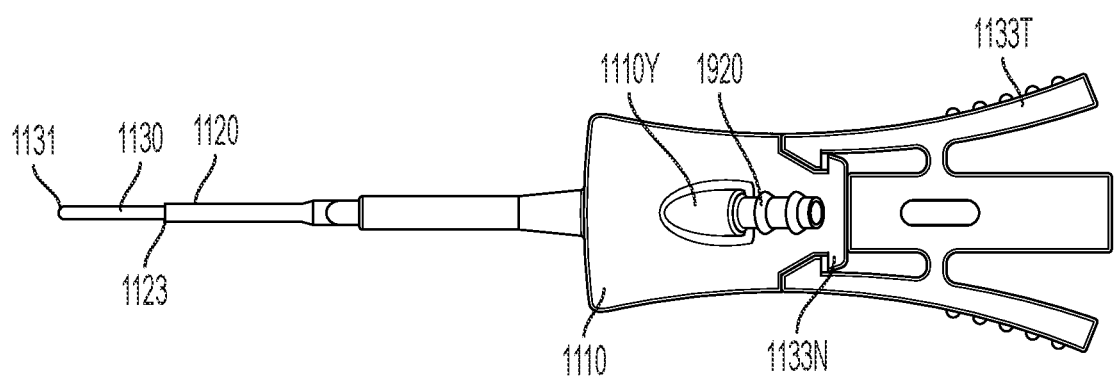
FIG. 21 is a detail view of the needle holder and the needle within the hub and outer lumen of the alternate embodiment as shown in FIGS. 19A/B and FIG. 20.
Figure 22A:
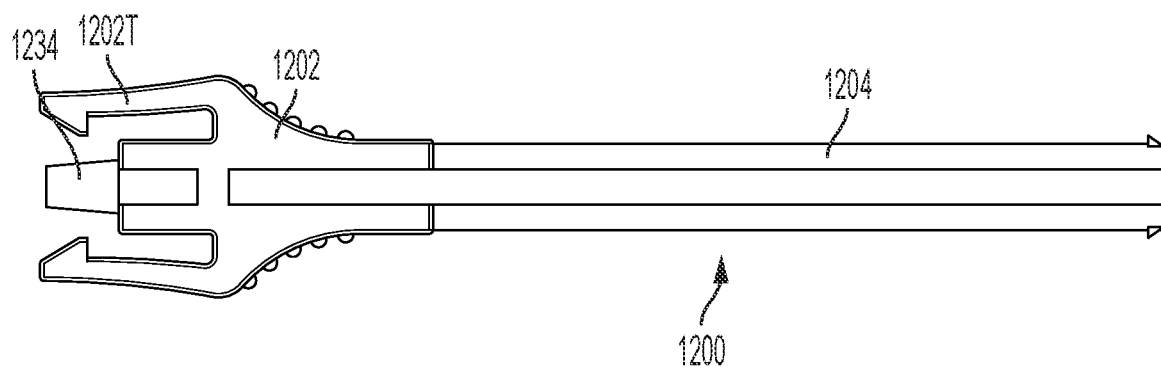
FIG. 22A is a detail view of a thump slide housing and inner lumen of the alternate embodiment as shown in FIGS. 17A/B and 18.
Figure 22B:
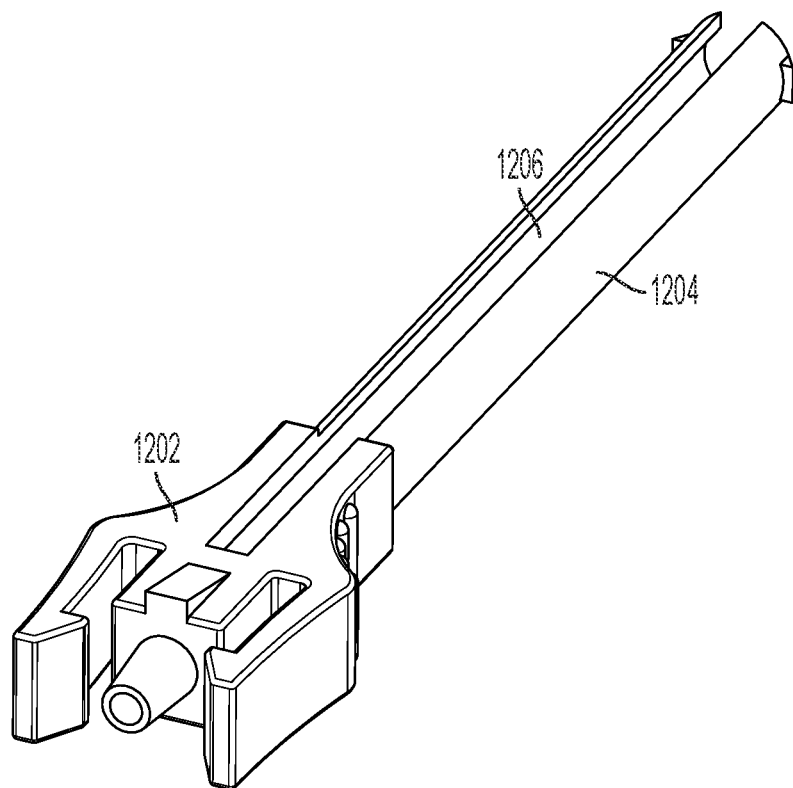
FIG. 22B is a perspective view of the thump slide housing and elongated member shown in FIG. 22A.

Referring to FIGS. 18-20, the alternate embodiment includes a needle member 1130 having a pointed end 1131 and a blunt end 1132. Needle 1130 is preferably held in position within needle holder 1133. Referring also now to FIG. 21, needle holder 1133 supporting needle 1130 is adapted to be inserted into end 1110b of housing 1110 through a seal 1111 (See also FIGS. 19A/B). The alignment of the needle holder with housing 1100 is ensured through to use of frustoconical element 1134. Additionally, seal 1111 may comprise a pair of opposing seals as shown in FIGS. 18 and 19A/B to ensure a proper seal when needle 1131 is inserted and later withdrawn. A seal cap 1136 is shown in FIG. 18 which holds seals 1111 as shown FIGS. 18 and 19A/B in place while needle passes through seals 1111.

In this manner, needle 1130 is permitted to pass through passageway 1901 of housing 1110 and outer lumen 1120. Needle holder 1133 is securely engaged to housing 1110 by tabs 1133T that engage and lock onto notches 1110N of housing 1110. The length of needle 1130 is selected so that when tabs 1133T engage and lock onto notches 1110N, pointed end 1131 of needle 1130 extends past end 1123 of outer lumen 1120.

Housing 1110 includes a Y-branch portion 1110Y defining a second passageway 1902. Tube 1170 is pushed onto end 1910 of Y-branch portion 1110Y and is held in position by ribs 1920. A clamp 1175 is placed along tubing 1170 to seal off tubing 1170 initially.

For insertion into a patient, an attendant presses end 1131 of needle 1130 against the target area 310 (FIG. 16) to break the skin and continued pressing causes end 1131 of needle 1130 and outer lumen member 1120 to enter an arteriovenous fistula of the patient. When the end 1131 enters the arteriovenous fistula, a flash of blood 330 flows into needle 1130, out the relief port 1131H (FIG. 20) of needle 1130, into passageway 1902 of Y-branch portion 110Y and into tubing 1170. Clamp 1175 prevents the blood from exiting tubing 1170 during this initial placement of the catheter. However, blood is observed within tubing 1170 upstream clamp 1175. (See, e.g., FIG. 16, Step 3.). Once the flash of blood is observed, tabs 1133T are compressed lifting the tabs away from notches 1110N thereby dis-engaging needle holder 1133 from housing 1110 and permitting needle holder 1133 and needle 1130 to be withdrawn from passageway 1901. Passageway 1901 at end 1110b of housing 1110 is then temporarily resealed by seals 1111. Once needle 1130 is removed, housing 1110 may be secured to the target area 310 using one or more of the attachment features such as 116a, 116b, 118 as shown FIG. 9. (See, e.g., FIG. 16, Step 5).

Figure 24:
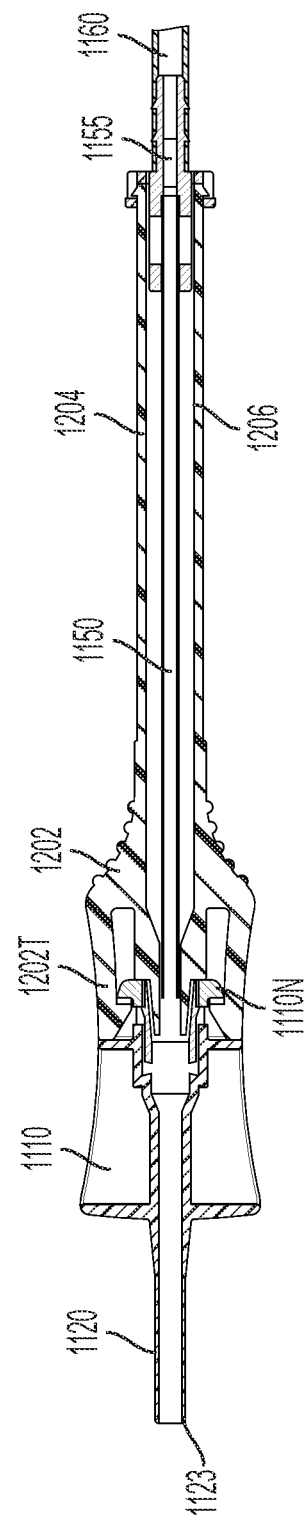
FIG. 24 is a detailed view of the thump slide housing and inner lumen in a retracted position within the hub and outer lumen of the alternate embodiment shown in FIGS. 19A/B and FIG. 22A.

Referring now to FIGS. 17B, 18, and 22-24, the installation of the inner lumen 1150 will be described. The alternate embodiment includes thump slide housing 1200 having a holder 1202 at one end with tabs 1202T. Housing 1200 includes an open elongated member 1204 having an open slot 1206 along its length. Located within elongated member 1204 is an inner lumen 1150. Inner lumen 1150 has a first open end 1152 and a second open end 1154 which is attached at the outer surface of lumen 1150 to thump slide 1155. Thus, passageway 1157 extends from the end of lumen 1150 at thump slide 1155 and continues through thump slide 1155 exiting out the back end 1161 of thump slide 1155. Ribs 1171 are found at the back end 1161 permitting the placement of tubing 1160. In this manner, there is an open passageway from tubing 160 through passageway 1157 and into the open ends 1152/1154 of inner lumen 1150. When the thump slide is fully retracted as shown in FIGS. 17A and 24, inner lumen 1150 rests completely within elongated member 1204.

For the installation of the inner lumen 1150, reference is now made to FIGS. 17B, 18, and 22-25. Thump slide holder 1202 is attached to housing 1110 by compressing tabs 1202T permitting tabs 1202T to lock onto notches 1110N. Slide holder 1202 is properly aligned within housing 1110 through the use of a frustoconical element 1234. Once thump slide holder 1202 is mated with housing 1110 the opening of elongated member 1204 is axially aligned with passageway 1901 of outer lumen 1120, and thump slide 1155 may be advanced. Since thump slide 1155 moves within elongated member 1204 along open slot 1206, it advances inner lumen 1150 into passageway 1901 piercing seals 1111. As the diameter of inner lumen 1150 is less than the diameter of outer lumen 1120 and the length of elongated member 1204 is selected so that when thump slide 1155 is fully extended from the positions shown in FIG. 17A to FIG. 17B by a distance X as shown in FIG. 17B, or from FIG. 24 to FIG. 25, inner lumen 1150 advances within passageway 1901 and extends past end 1123 of outer lumen 1120 into the vein or artery of the patient.

Preferably, end 1152 of inner lumen 1150 extends between about 5 mm to about past end 1123 of outer lumen 1120, more preferably between about 10 mm to about past end 1123 of outer lumen 1120, and most preferably between about 15 mm to about 25 mm past end 1123 of outer lumen 1120. In order to gauge to amount of insertion of end 1152 of inner lumen 1150 past end 1123 of outer lumen 1120, the alternate embodiment may include markings on the outer surface of elongated member 1204 similar to that shown, for example, in FIGS. 4, 7A, 8B, and 12 and discussed above.

Once end 1152 of inner lumen member 1150 is inserted past end 1123 of the outer lumen 1120 to the desired depth, inner lumen member 1150 and outer lumen member 1120 are primed to effect blood flow (see, e.g., FIG. 16, Step 7). Tubes 1160 and 1170 are temporarily clamped (clamps 1165 and 1175) to temporarily prevent blood flood from the arteriovenous fistula (See, e.g., FIG. 16, Step 8).

Tubes 1160, 1170 are connected to a dialysis machine 180, with tube 1160 connected to the inner lumen 1150 configured to pass blood from the machine 180 into the patient, and tube 1170 connected to the outer lumen 1120 configured to pass blood to the machine 180 from the patient (See, e.g., FIG. 16, Step 9). The tubes 1160, 1170 are then unclamped to permit blood flow accordingly (See, e.g., FIG. 16, Step 10), and the tourniquet 320 is removed (See, e.g., FIG. 16, Step 11). The blood replacement process then continues for a desired or recommended amount of time.

Figure 25:
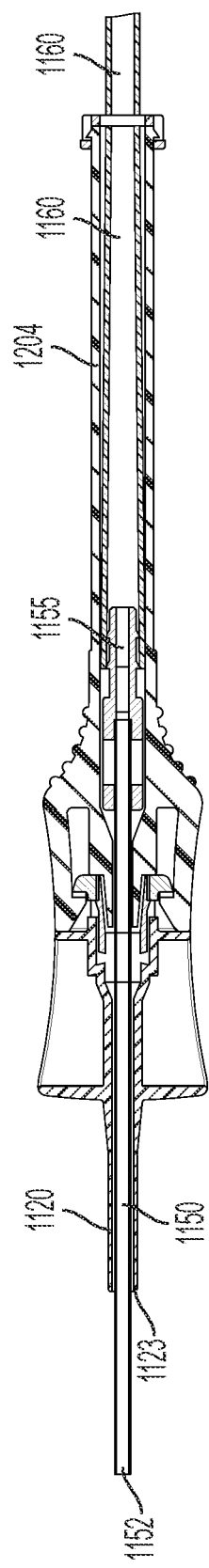
FIG. 25 is a detailed view of the thump slide housing and inner lumen in an extended position within the hub and outer lumen of the alternate embodiment shown in FIGS. 19A/B and FIG. 22A.

Once the blood replacement process has continued for the desired or recommended amount of time, dialysis machine 180 is deactivated, and tubes 1160, 1170 are clamped and then disconnected from machine 180. Then, as shown in FIG. 25, inner lumen 1150 is retracted by moving thump slide 1155 back within elongated member 1204, and elongated member 1204 is removed from housing 1110. Housing member 1110/outer lumen 1120 are then removed from the target area 310 of the patient. Finally, the wound is sterilized and bandaged.

Figure 26:
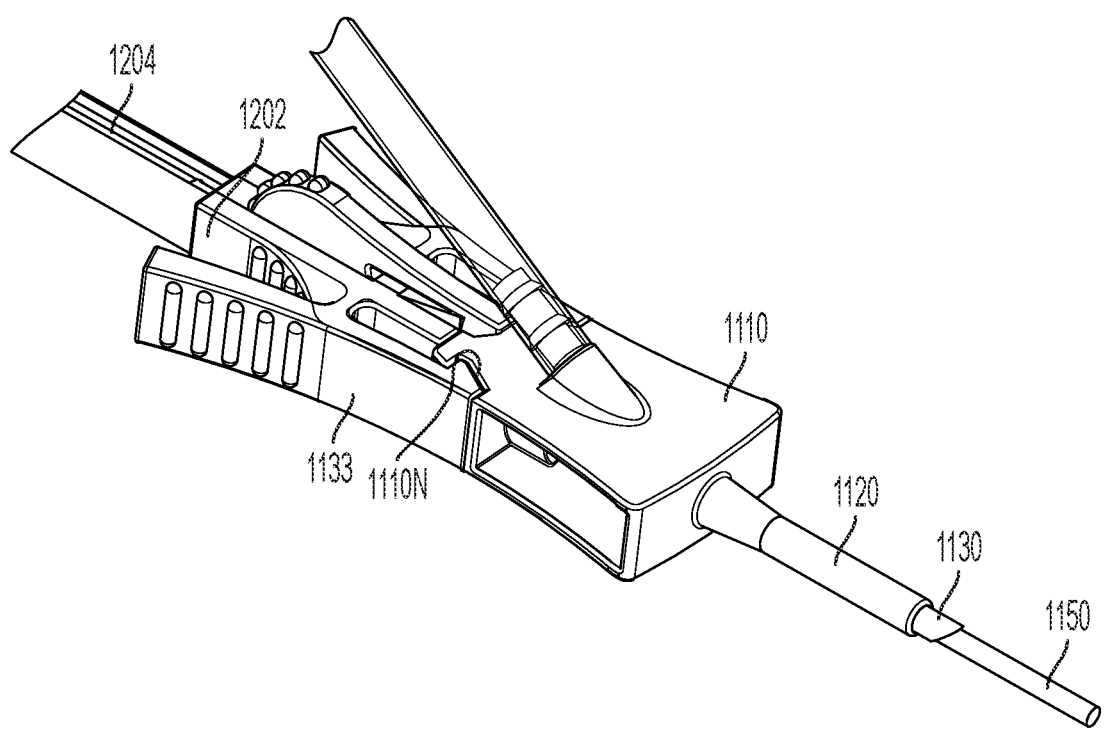
FIG. 26 is a detail view of yet another alternate embodiment of the present invention with the needle holder and needle remaining within the invention and thumb slide housing and elongated member shown in FIGS. 24 and 25 being attached to the opposite end of the needle holder from the needle.

In this manner the invention is an integrated catheter that permits retrieval and delivery of blood through a single injection site Referring to FIG. 26, it may be desirable to leave needle 1130 within the patient during dialysis. In that event, the outer diameter of needle 1130 is selected to be less than the inner diameter of outer lumen 1120 and the inner diameter of needle 1130 is selected to be more than the outer diameter of inner lumen 1150. Additionally, needle holder 1133 would be manufactured to accommodate an open-ended needle and would include a passageway out the back end of holder 1133 and notches similar to 1110N to engage tabs 1202T of thump slide holder 1202. Additionally, inner lumen 1120 and elongated member 1202 would be manufactured long enough to accommodate a longer inner lumen 1150 since inner lumen 1150 needs to also span the entire length of needle holder 1133 since it remains in place. As shown in FIG. 26, needle holder 1133 in inserted into housing 1110 and thump slide holder 1202 is attached to the back oh needle housing 1133, so that all three housings 1110/1133/1202 are in alignment and used as an integrated catheter assembly in the fashion described above except that the needle holder 1133 and needle 1130 remain in place behind the housing 1110 while the inner lumen 1150 is extended through the housing 1110 past the outer lumen 1120.

Referring now to FIGS. 27-33, another alternate embodiment of the present invention is shown. Numerals in these figures usually correspond to similar elements in the preferred embodiment but with a 2000 series prefix. However, all element numbers in this alternate embodiment may not have a corresponding element in the preferred embodiment. Thus, all element numbers in this alternate embodiment may not follow the 2000 prefix convention mentioned above.

Referring now to FIGS. 27-30, integrated catheter device 2100 includes a hub or housing member 2110, a needle assembly 2200, and a hub assembly 2300.

Figure 27:
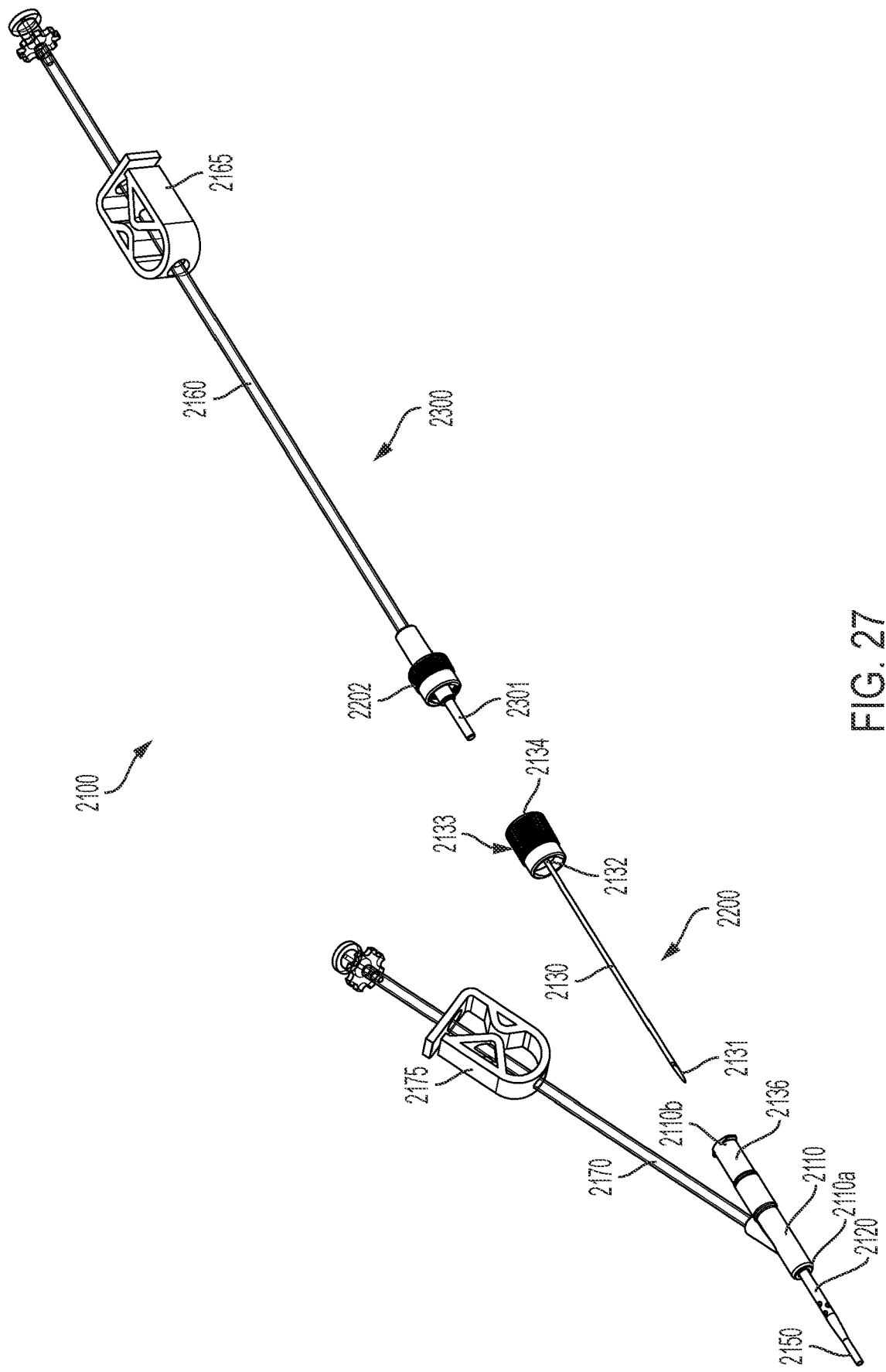
FIG. 27 is a perspective view of another alternate embodiment of the integrated catheter assembly.
Figure 28:
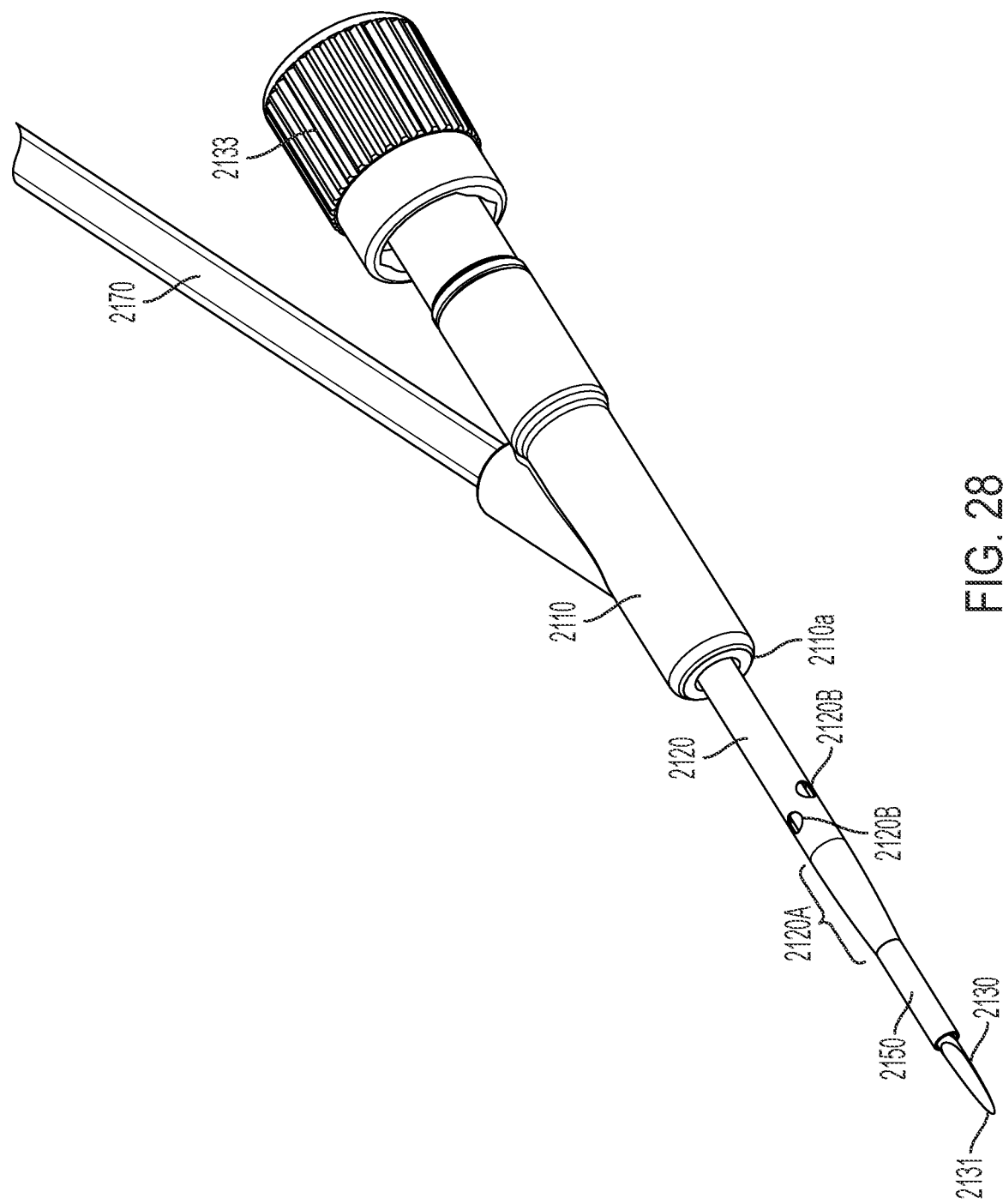
FIG. 28 is a perspective view of a portion of the alternate embodiment generally shown in FIG. 27.
Figure 29A:
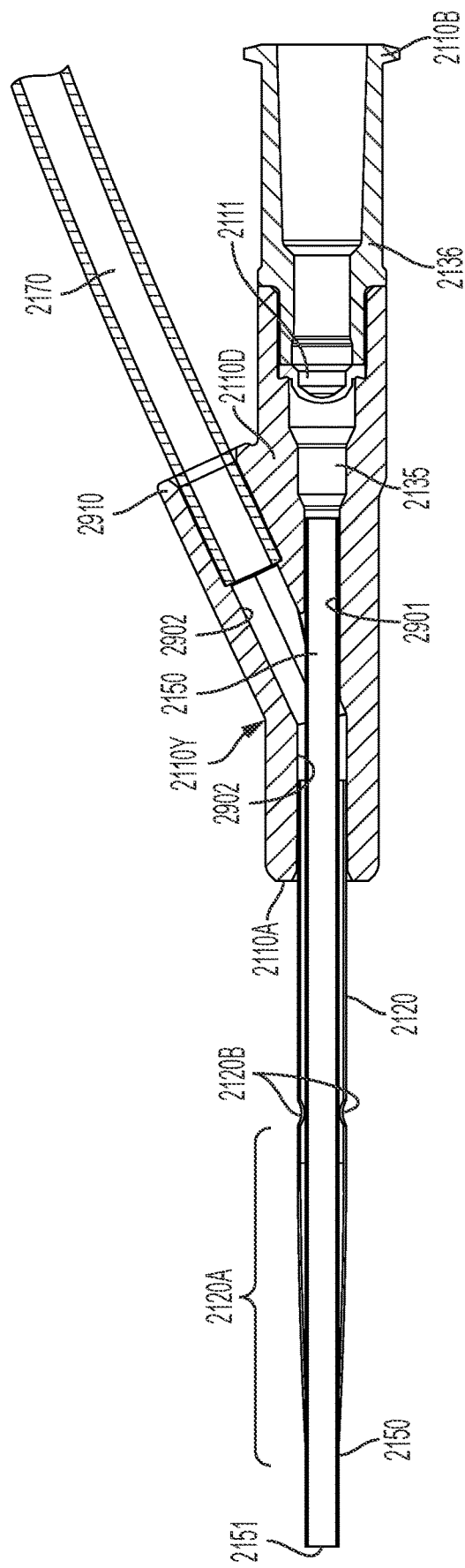
FIG. 29A is a cross-sectional view of the portion of the invention shown in FIG. 28.

Referring now to FIGS. 27, 28, and 29A, housing member 2110 has a first end 2110A and an opposing second end 2110B. An outer lumen member 2120 extends from at least the first end 2110A of housing 2110. Outer lumen 2120 may be integrally molded as a part of housing 2110. Housing 2110 and outer lumen 2120 define an open passageway 2902 extending therethrough. An inner lumen 2150 is supported within housing 2110 and is co-axially oriented within outer lumen 2120. Referring to FIG. 29A, inner lumen 2150 is proximally supported within housing 2110 proximate end 2110B. Inner lumen forms a second passageway 2901 which extends from the distal end 2151 of inner lumen 2150 through the inner diameter of inner lumen 2150 into body 2110D of housing 2110.

Figure 30:
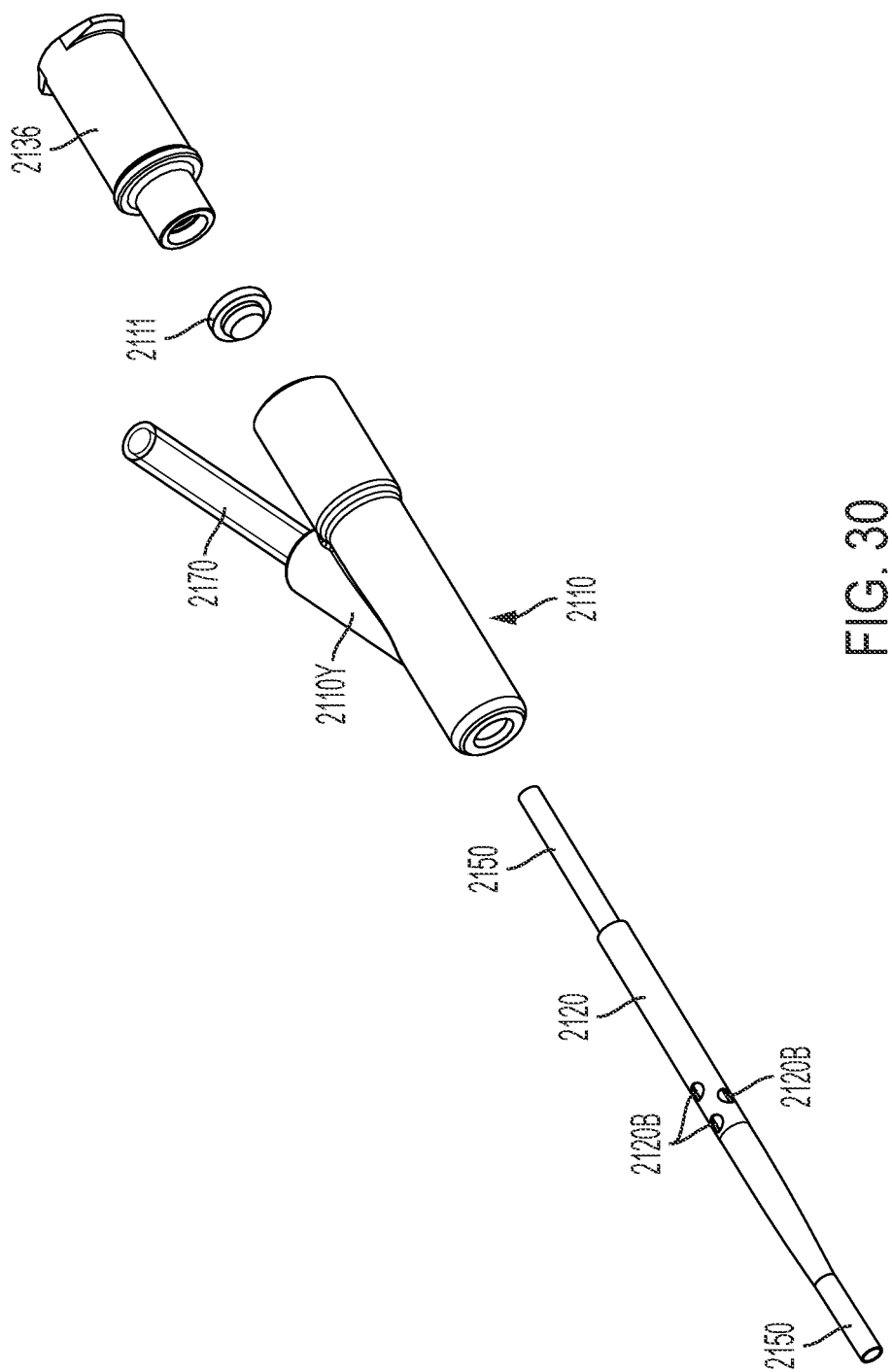
FIG. 30 is an exploded view of a portion of the perspective view shown in FIG. 28.

Referring still to FIGS. 27 and 28, the needle assembly 2200 includes a needle 2130 having a pointed end 2131 and a blunt end 2132. Needle 2130 is preferably held in position within needle holder 2133. Needle holder 2133 supporting needle 2130 is adapted to be inserted into end 2110B of housing 2110 through a seal 2111 (See also FIGS. 29A and 30). Referring to FIG. 29A, the alignment of needle holder 2133 within housing 2110 is ensured by frustoconical element 2135. Needle holder 2133 is firmly seated within housing 2110 by luer 2134. Additionally, seal 2111 is supported within housing 2110 as shown in FIGS. 29A and 30. Seal 2111 serves to seal passageway 2901. Seal 2111 is available from the Minivalve Company of Cleveland, OH, www.minivalve.com, model DO 030.002 SD. Seal 2111 includes an indention to accept the needle 2130 when it is punctured by end 2131 of needle 2130 and then seal around needle 2130 as needle 2130 is advanced within housing 2110 and into inner lumen 2150. Seal 2111 is held firmly within housing 2110 by seal retainer and luer connector 2136. (FIG. 30). Thus, needle 2130 is located co-axially within inner lumen 2150 and inner lumen is located co-axially within outer lumen 2120.

In this manner, when integrated catheter device 2100 is initially assembled before insertion into the target area of the patient, needle 2130 punctures seal 2111 and passes through passageway 2902 of housing 2110 and within inner lumen 2150/outer lumen 2120. Needle holder 2133 is securely engaged to housing 2110 by luer 2134 engaging seal retainer/luer connector 2136. The length of needle 2130 is selected so that when luer 2134 secures needle holder 2133 onto housing 2110, the pointed end 2131 of needle 2130 extends past end 2151 of inner lumen 2150. Preferably, tip 2131 extends past end 2151 of inner lumen 2150 between about 6 mm and 1 mm and preferably between about 4 mm and 1 mm, and most preferably about 2 mm. Device 2100 may be provided to a health provider in a package with needle assembly 2200 fully supported within housing 2110.

Referring now to FIGS. 28, 29A/29B, and 30, housing 2110 includes a Y-branch portion 2110Y defining passageway 2901 extending laterally away from passageway 2901. Tube 2170 is pushed onto end 2910 of Y-branch portion 2110Y. Clamp 2175 is placed along tubing 2170 to seal off tubing 2170 initially.

Referring still to FIGS. 29A and 29 B, outer lumen 2120 is secured within housing 2110 at end 2110A, and it may extend further into the housing within passageway 2902. Inner lumen 2150 is supported co-axially within passageway 2901 within body portion 2110D of Y-branch 2110Y. Inner lumen extends from end 2151 and terminates proximate frustoconical element 2135 within body portion 2110D of housing 2110. In this manner the inner lumen extends into body portion 2110D past Y-branch 2110Y. Thus passageway 2902 is sealed off from passageway 2901.

The inner diameter of outer lumen 2120 is greater than the outer diameter of the inner lumen 2150. Preferably, the inner diameter of the outer lumen 2120 is approximately 2.41 mm and the outer diameter of the inner lumen 2150 is approximately 2.16 mm leaving an annular space 2901A of about 0.13 mm. The gauge of needle 2130 is selected to fit within the inner diameter of inner lumen 2150, such as an 18 G needle.

Figure 29B:
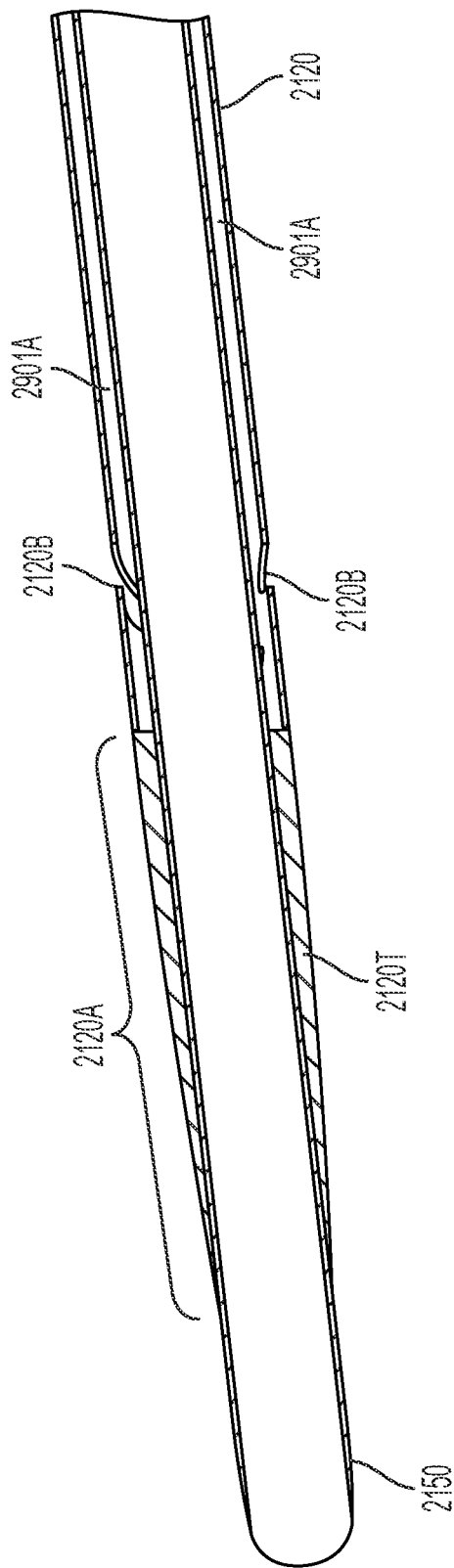
FIG. 29B is a cross-sectional view of the distal ends of the outer lumen 2110 and the inner lumen 2150 as shown in FIG. 28.
Figure 29C:
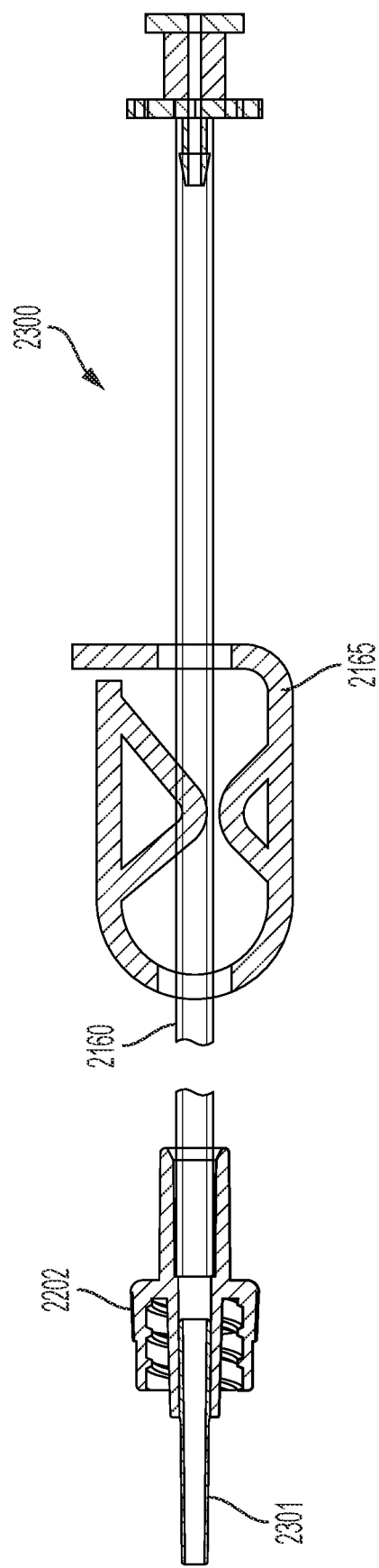
FIG. 29C is a cross-sectional view of the hub assembly 2300 as shown in FIG. 27.

Referring now to FIGS. 29A and 29B, outer lumen 2120 includes at least one aperture 2120B distal housing 2110. Preferably, there are at least two apertures 2120B and, more preferably, about 4 to 5 apertures 2120B spaced circumferentially around the needle or staggered in rows about the circumference. Apertures 2120B are preferably between about 1.5 mm and 1 mm in diameter and, more preferably, about 1.28 mm in diameter. If staggered in two or more rows around the circumference of outer lumen 2120 each aperture 2120B is preferable 90° staggered from an adjacent aperture 2120B (FIG. 30) and they are spaced about 1 mm to 3 mm between circumferential rows and most preferable about 1.5 mm.

Referring now to FIG. 29B, the outer diameter of outer lumen 2120 gradually tapers within region 2120A until the annular space 2901A between the inner diameter of the outer lumen 2120 and the outer diameter of the inner lumen 2150 is eliminated within region 2120A. Alternatively, a taper plug 2120T may be used to seal the annular space 2901A as shown in FIG. 29B.

In this manner, two passageways are created. The passageway which provides for the flow of blood through apertures 2120B along with annular region 2901A back into housing 2110 where it is displaced into passageway 2902 and passes through Y-branch portion 2110Y and out tubing 2170. Another passageway 2901 which extends from the end 2151 of inner lumen 2150 into passageway 2901 within housing 2110 and past seal 2111 as shown in FIG. 29A.

Figure 31:
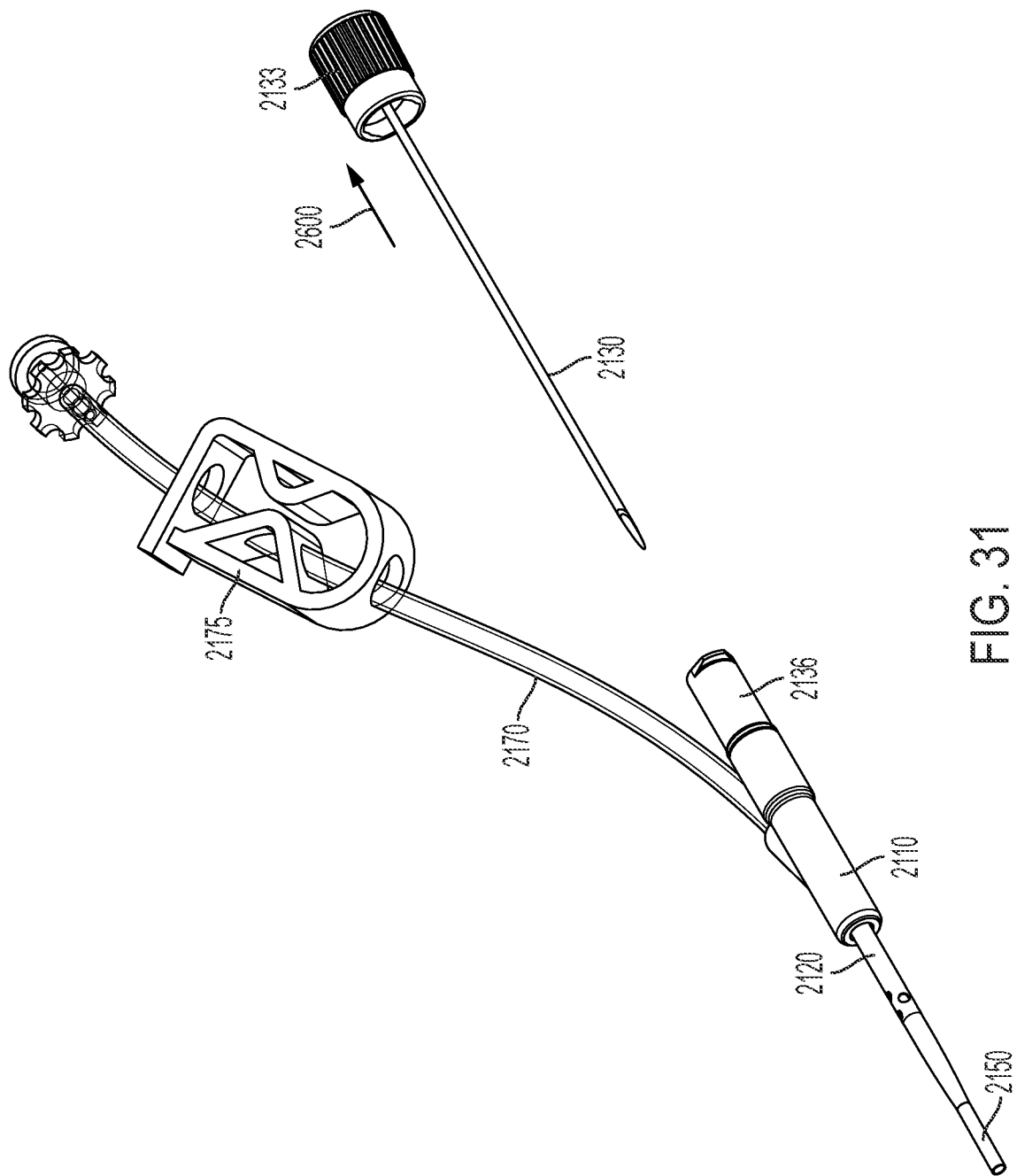
FIG. 31 is a perspective view of a portion of the embodiment shown in FIG. 27.
Figure 32:
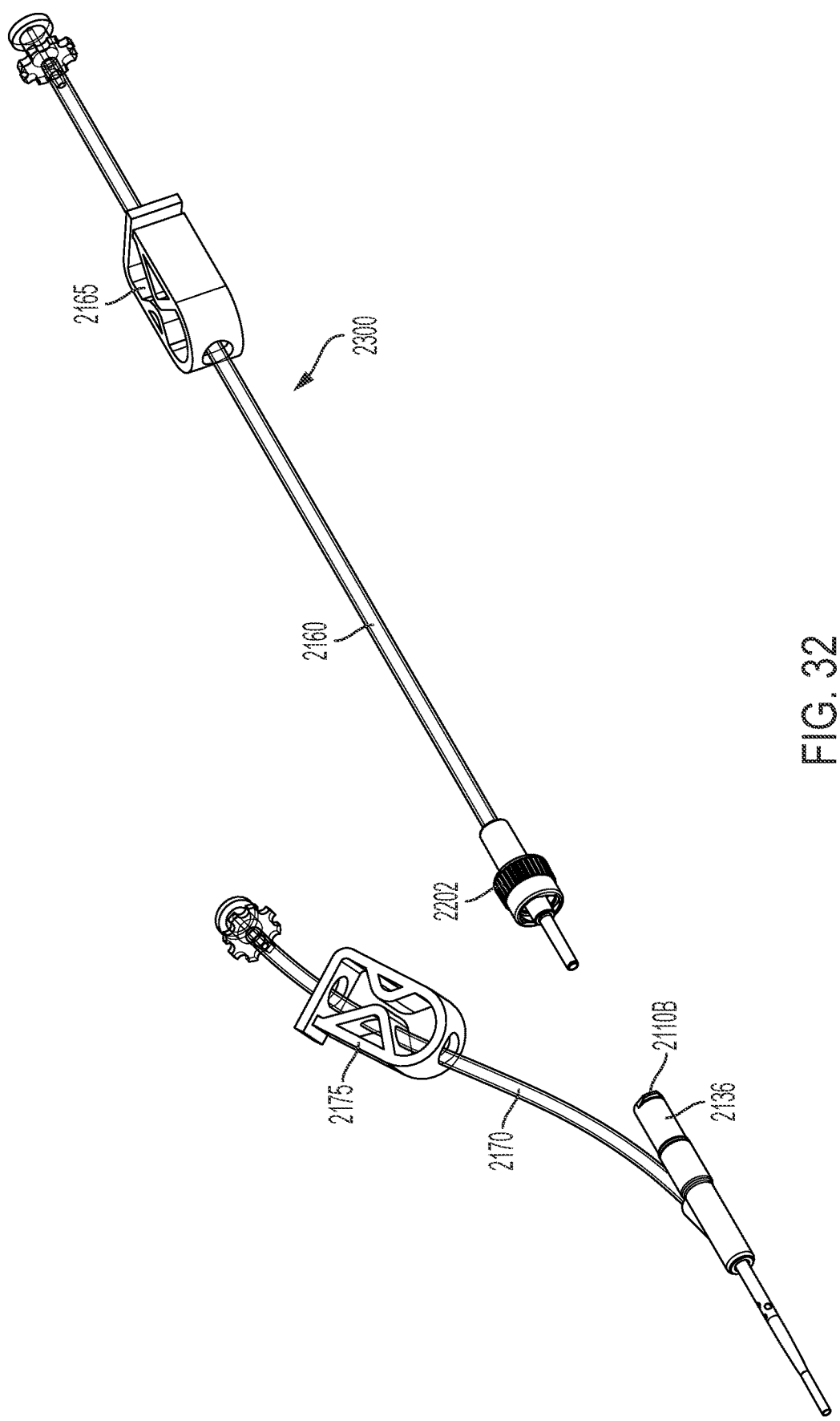
FIG. 32 is another perspective view of a portion of the embodiment shown in FIG. 27.
Figure 33:
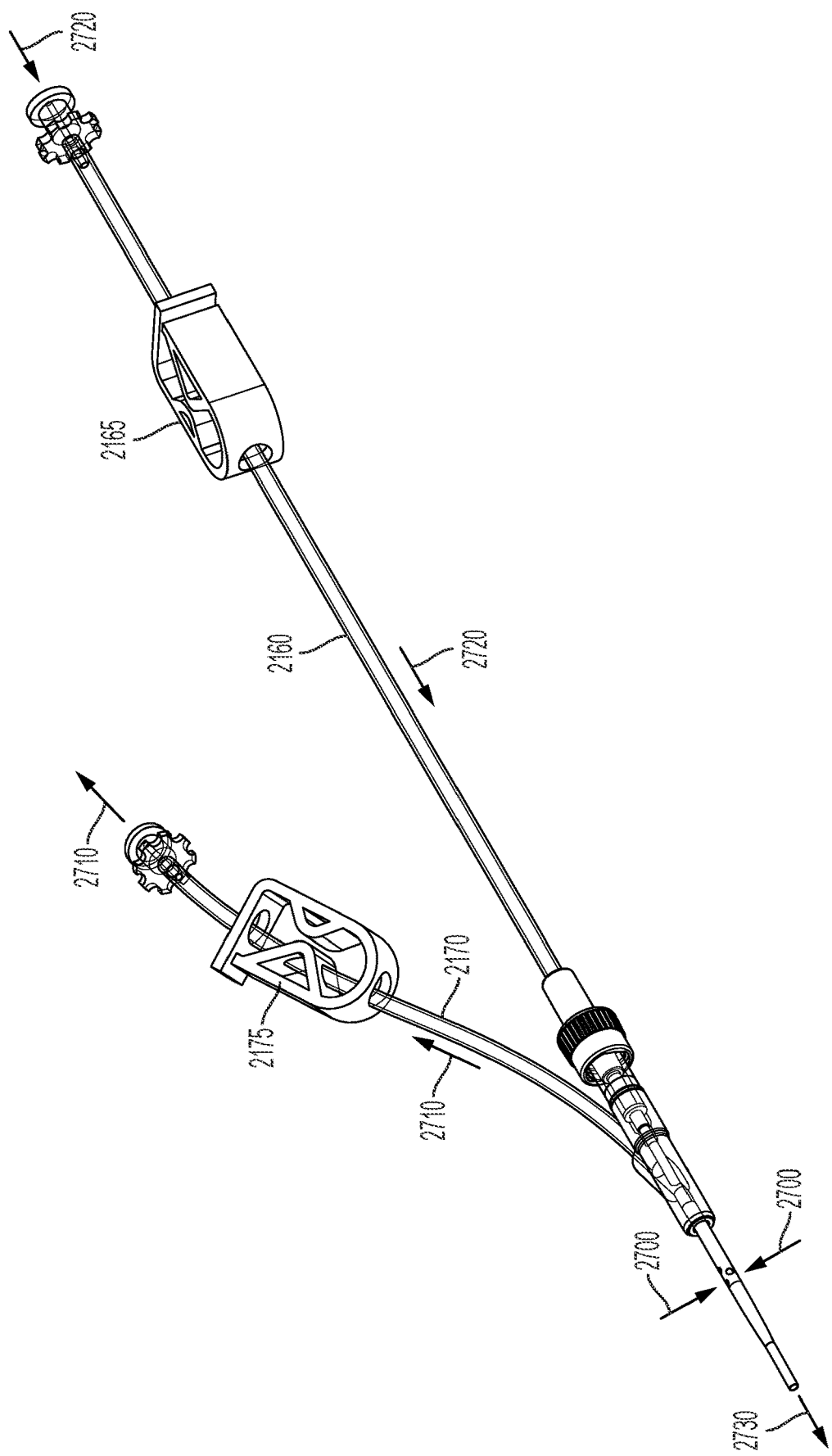
FIG. 33 is a perspective view of the alternate embodiment shown in FIG. 27 with arrows illustrating the flow of blood.

Still referring to FIGS. 28, 29A and 29B, an attendant presses tip 2131 of needle 2130 against the target area 310 (FIG. 16) to break the skin and continues pressing causing needle 2130, inner lumen 2150, and outer lumen member 2120 to enter an arteriovenous fistula of the patient. When tip 2131 enters the arteriovenous fistula, blood enters annular region 2901A through apertures 2120B and flows downstream into housing 2110 and out through passageway 2902 of Y-branch portion 2110Y and into tubing 2170. Clamp 2175 prevents the blood from exiting tubing 2170 during this initial placement of the catheter. However, blood is observed within tubing 2170 upstream clamp 2175. (See, e.g., FIG. 16, Step 3.). Referring now to FIGS. 31 and 32, once the flash of blood is observed, lure 2134 (FIG. 27) is rotated disengaging needle holder 2133 from housing 2110 and permitting needle holder 2133 and needle 2130 to be withdrawn from passageway 2901. Passageway 2901 at end 2110B of housing 1110 is then temporarily resealed by seal 2111. Once needle 2130 is removed, housing 2110 may be secured to the target area 310 using one or more of the attachment features such as 116*a*, 116*b*, 118 as shown FIG. 9. (See, e.g., FIG. 16, Step 5).

Referring now to FIGS. 27, 29C, 32, and 33, the installation of hub assembly 2300 will be described. Return assembly 2300 includes lure assembly 2202 at the distal end of hub assembly 2300. Luer assembly 2202 also includes a hollow plunger 2301 which is advanced into seal retainer/lure connector 2136 and penetrates seal 2111. Since plunger 2301 is hollow it establishes fluid communication with passageway 2901. Tubing 2160 is attached at one end to luer assembly 2202. A clamp 2165 is included which serves to prevent flow until released. Thus, once hub assembly 2300 is inserted within end 2110B of housing 2110, it establishes continuous fluid communication between the interior of tubing 2160 through housing 2110 and inner lumen 2120 along passageway 2901.

Once hub assembly 2300 is fully secured within housing 2110 and establishes a fluid communication with passageway 2901, inner lumen member 2150 and outer lumen member 2120 are primed to effect blood flow (see, e.g., FIG. 16, Step 7). Tubes 2160 and 2170 are temporarily clamped (clamps 2165 and 2175) to temporarily prevent blood flood from the arteriovenous fistula (See, e.g., FIG. 16, Step 8).

Tubes 2160, 2170 are connected to a dialysis machine 180, with tube 2160 connected to the inner lumen 2150 configured to pass blood from the machine 180 into the patient, and tube 2170 connected to the outer lumen 2120 configured to pass blood to the machine 180 from the patient (See, e.g., FIG. 16, Step 9). The tubes 2160, 2170 are then unclamped to permit blood flow accordingly (See, e.g., FIG. 16, Step 10), and the tourniquet 320 is removed (See, e.g., FIG. 16, Step 11). The blood replacement process then continues for a desired or recommended amount of time.

Once the blood replacement process has continued for the desired or recommended amount of time, dialysis machine 180 is deactivated, and tubes 2160, 2170 are clamped and then disconnected from machine 180. Housing member 2110, outer lumen 2120, and inner lumen 2150 are then removed from the target area 310 of the patient. Finally, the wound is sterilized and bandaged.

It is to be understood that the foregoing illustrative exemplary embodiments have been provided merely for the purpose of explanation and are in no way to be construed as limiting of the present general inventive concept. Words used herein are words of description and illustration, rather than words of limitation. In addition, the advantages and objectives described herein may not be realized by each and every exemplary embodiment practicing the present general inventive concept. Further, although the present general inventive concept has been described herein with reference to particular structure, steps and/or exemplary embodiments, the present general inventive concept is not intended to be limited to the particulars disclosed herein. Rather, the present general inventive concept extends to all functionally equivalent structures, methods and uses, such as are within the scope of the appended claims. Those skilled in the art, having the benefit of the teachings of this specification, may affect numerous modifications thereto and changes may be made without departing from the scope and spirit of the present general inventive concept.

What is claimed is:

1. An integrated catheter assembly, comprising:
a housing member having a first end and a second end;
an elongated outer lumen member, having a first and second end, extending from the first end of the housing member;
a non-removable elongated inner lumen member, having a first and second end, also adapted to be supported at the second end of the inner lumen member within the first end of the housing member, and positioned co-axially within the outer lumen member;
a removeable needle assembly comprising:
a holder assembly, and
a needle supported by said holder assembly and adapted to be removably inserted through the housing member and into the inner lumen member, said first end of the needle extending past the first end of the inner lumen member;
a hub assembly, having a first end and a second end, and an inner passageway, said first end of said hub assembly adapted to engage the second end of the housing member following removal of the needle assembly; and
a seal supported within the housing member,
wherein said outer lumen member includes at least one aperture proximate the first end of said outer lumen member and distal said housing member defining the commencement of a first passageway between the outer diameter of the inner lumen member and the inner diameter of the outer lumen member and wherein the first end of the outer lumen member is sealed proximate the first end of the inner lumen member distal said housing member, and
wherein the interior of the inner lumen member forms a second passageway extending from the first end of the inner lumen member distal said housing member, through said housing to said seal, and
wherein the first and second passageways permit the simultaneous flow of fluids from a body and into a body from a single target site.

2. The catheter assembly of claim 1, further comprising:
said hub assembly includes a plunger supported co-axially with the inner lumen member within the housing assembly so that as said hub assembly engages the second end of the housing member said plunger pierces said seal establishing fluid communication between the inner passageway of said hub assembly with the second passageway defined by the inner lumen member.

3. The integrated catheter assembly of claim 1, further comprising at least one adhesive flap contoured to approximate a curvature of an arm.

4. An integrated catheter assembly, comprising:
a housing member having a first end, a second end, and a lateral end;
an elongated outer lumen member, having a first and second end and inner and outer diameters, said outer lumen member extending proximate the first end of the housing member;
a non-removeable elongated inner lumen member, having a first end and a second end and inner and outer diameters, said inner lumen member extending from the housing member and supported at the second end of the inner lumen member within said housing member, said inner lumen having an outer diameter smaller than the inner diameter of the outer lumen and positioned co-axially within the outer lumen member, the first end of the inner lumen member extending past the first end of the outer lumen member;
a removeable needle assembly comprising a holder assembly and a needle, having an outer diameter less than the inner diameter of the inner lumen member and supported by said holder assembly, said needle assembly adapted to be removably inserted through the housing member and into the inner lumen member, said first end of the needle extending past the first end of the inner lumen member;
a hub assembly, having a first end and a second end and an inner passageway, said first end of said hub assembly adapted to engage the second end of the housing member following removal of the needle assembly;
a seal supported within the housing member; and
said hub assembly further includes a plunger supported co-axially with the inner lumen member within said hub assembly so that as said hub assembly engages the second end of the housing member said plunger pierces said seal following removal of the needle assembly,
wherein said outer lumen member includes at least one aperture proximate the first end of said outer lumen member and distal said housing member defining the commencement of a first passageway between the outer diameter of the inner lumen member and the inner diameter of the outer lumen member and wherein the first end of the outer lumen member is sealed distal proximate the first end of inner lumen member, and
wherein the interior of the inner lumen member forms a second passageway extending from the first end of the lumen member distal said housing to said inner passageway of the hub assembly and the pierced seal, establishing an open fluid communication out the second end of the housing, and
wherein the first and second passageways permit the simultaneous flow of fluids from a body and into a body.

5. The integrated catheter assembly of claim 4, further comprising an outflow tube coupled in fluidic communication with the first passageway.

6. The integrated catheter assembly of claim 4, further comprising an inflow tube coupled in fluidic communication with the second end of said hub assembly.

7. The integrated catheter assembly of claim 4, further comprising at least one adhesive flap contoured to approximate a curvature of an arm.

8. An integrated catheter assembly, comprising:
a housing member having a generally Y-configuration and a first end, a second end, and a third end opposite the first end, defining a first passageway from the first end of the Y-configuration through the second end of the Y-configuration, and a second passageway from the first end of the Y-configuration through the third end of the Y-configuration;
an elongated outer lumen member, having a first and second end and inner and outer diameters, said outer lumen member extending from at least the first end of the housing member;
an elongated inner lumen member, having a first end and a second end and inner and outer diameters, said inner lumen member extending from at least the first end of the housing member and supported at the second end of the inner lumen member proximate the first end of the housing member, said inner lumen having an outer diameter smaller than the inner diameter of the outer lumen and positioned co-axially within the outer lumen member, the first end of the inner lumen member extending past the first end of the outer lumen member;
a removeable needle assembly comprising:
a holder, having a first end and a second end and adapted to engage the third end of the housing member, and
a hollow needle, having a first end and a second end, said outer diameter of said needle being less than the inner diameter of the inner lumen member and supported by said holder and adapted to be removably inserted through the housing member and into the inner lumen member, said first end of the needle extending past the first end of the inner lumen member;
a seal supported within the second passageway within the housing member;
a hub assembly, having a first end and a second end and an inner passageway, said hub assembly adapted to engage the third end of the housing member following removal of the needle assembly so that said inner passageway and said second passageway are in fluid communication,
wherein said outer lumen member includes at least one aperture proximate the first end of said outer lumen member and distal said housing and wherein the first end of the outer lumen member is sealed proximate the first end of said outer lumen member defining the commencement of the first passageway from said at least one aperture distal said housing between the inner diameter of the outer lumen member and the outer diameter of the inner lumen member to the first end of the Y-configuration and through the second end of the Y-configuration, and
wherein the interior of the inner lumen member defines the second passageway extending from the first end of the inner lumen member distal said housing to the first end of the Y configuration and through to the third end of the Y-configuration permitting the simultaneous flow of fluids through the first and second passageways from a single target site.

9. The integrated catheter assembly of claim 8 wherein said hub assembly includes a plunger supported co-axially with the inner lumen member so that as said hub assembly engages the third end of the Y-configuration housing member said plunger pierces said seal establishing fluid communication between the inner passageway of said hub assembly with the passageway defined by the inner diameter of the inner lumen member further defining the second passageway.

10. The integrated catheter assembly of claim 8, further comprising an outflow tube coupled in fluidic communication with the first passageway.

11. The integrated catheter assembly of claim 8, further comprising an inflow tube coupled in fluidic communication with the second passageway.

12. The integrated catheter assembly of claim 8, further comprising at least one adhesive flap contoured to approximate a curvature of an arm.

13. An integrated catheter assembly, comprising:
a housing member having a first end, a second end, and a lateral end, defining a first passageway from the first end through the second end of the housing member and a second passageway from the first end through the lateral end of the housing member;
an elongated outer lumen member, having a first and second end and inner and outer diameters, said outer lumen member extending from the first end of the housing member and supported within the housing member wherein said outer lumen member includes at least one aperture proximate the first end of said outer lumen member defining the commencement of said second passageway;
a non-removable elongated inner lumen member, having a first end and a second end and inner and outer diameters, said inner lumen member extending from the first end of the housing member and supported at the second end of the inner lumen member within the housing member co-axially within the outer lumen, said inner lumen having an outer diameter smaller than the inner diameter of the outer lumen, the first end of the inner lumen member extending past the first end of the outer lumen member;
a removeable needle assembly comprising a holder, having a first end and a second end and adapted to engage the second end of the housing member, and a needle, having a first end and a second end, the outer diameter of the needle being less than the inner diameter of the inner lumen member and adapted to be removably inserted through the housing member and into the inner lumen member, said first end of the needle extending past the first end of the inner lumen member;
a seal supported within the first passageway within the housing member; and
a hub assembly having an inner passageway and adapted to engage the second end of the housing member following removal of the needle assembly so that said inner passageway and said first passageway are in fluid communication, said hub assembly includes a plunger to pierce said seal establishing fluid communication between the inner passageway of said hub assembly with the passageway defined by the inner diameter of the inner lumen member,
wherein the first end of the outer lumen member is sealed proximate to the first end of said outer lumen member distal said at least one aperture to the first end of the inner lumen member defining the commencement of the second passageway from said at least one aperture distal said housing between the inner diameter of the outer lumen member and the outer diameter of the inner lumen member to the first end of the housing member and through the lateral end of the housing member, and wherein the interior of the inner lumen member defines the first passageway extending from the first end of the inner lumen member distal said housing to the first end of the housing member, through the inner passageway of the housing member and the pierced seal and out the second end of the housing, and wherein the first and second passageways permit the simultaneous flow of fluids out of a body and back into a body.

14. The integrated catheter assembly of claim 13, further comprising an outflow tube coupled in fluidic communication with the second passageway.

15. The integrated catheter assembly of claim 13, further comprising an inflow tube coupled in fluidic communication with the first passageway.

16. The integrated catheter assembly of claim 13, further comprising at least one adhesive flap contoured to approximate a curvature of an arm.

* * * * *